(12) United States Patent
Tsai et al.

(10) Patent No.: US 11,085,062 B2
(45) Date of Patent: Aug. 10, 2021

(54) PROCESSES FOR PREPARING GLYCOPROTEIN-DRUG CONJUGATES

(71) Applicant: DEVELOPMENT CENTER FOR BIOTECHNOLOGY, Taipei (TW)

(72) Inventors: Shih-Chong Tsai, Taipei (TW); Chun-Chung Lee, Taipei (TW); Meng-Sheng Lee, Taipei (TW); Ching-Yao Chen, Taipei (TW); Shih-Hsien Chuang, Taipei (TW); Yi-Jen Chen, Taipei (TW); Win-Yin Wei, Taipei (TW)

(73) Assignee: DEVELOPMENT CENTER FOR BIOTECHNOLOGY, Taipei (TW)

( * ) Notice: Subject to any disclaimer, the term of this patent is extended or adjusted under 35 U.S.C. 154(b) by 0 days.

(21) Appl. No.: 16/470,807

(22) PCT Filed: Dec. 29, 2017

(86) PCT No.: PCT/US2017/068872
§ 371 (c)(1),
(2) Date: Jun. 18, 2019

(87) PCT Pub. No.: WO2018/126092
PCT Pub. Date: Jul. 5, 2018

(65) Prior Publication Data
US 2020/0087697 A1 Mar. 19, 2020

Related U.S. Application Data

(60) Provisional application No. 62/440,075, filed on Dec. 29, 2016.

(51) Int. Cl.
*C12P 21/00* (2006.01)
*A61K 47/68* (2017.01)
*C07K 16/32* (2006.01)

(52) U.S. Cl.
CPC ........ *C12P 21/005* (2013.01); *A61K 47/6817* (2017.08); *A61K 47/6849* (2017.08); *A61K 47/6851* (2017.08); *A61K 47/6883* (2017.08); *C07K 16/32* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 4,946,778 A | 8/1990 | Ladner et al. |
| 5,545,806 A | 8/1996 | Lonberg et al. |
| 5,545,807 A | 8/1996 | Surani et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,661,016 A | 8/1997 | Lonberg et al. |
| 7,416,858 B2 | 8/2008 | Heard et al. |
| 8,716,033 B2 | 5/2014 | Agnew et al. |
| 2004/0126838 A1 | 7/2004 | Heard |
| 2016/0106860 A1 | 4/2016 | Satomaa et al. |

FOREIGN PATENT DOCUMENTS

| | | |
|---|---|---|
| EP | 2563753 B3 | 5/2014 |
| JP | 2015-534996 A | 12/2015 |
| JP | 2016-538877 A | 12/2016 |
| WO | 2014/065661 A1 | 5/2014 |
| WO | 2014065661 A1 | 5/2014 |
| WO | 2014-164534 A1 | 10/2014 |
| WO | 2015032899 A1 | 3/2015 |
| WO | 2015/057063 A1 | 4/2015 |
| WO | 2015057064 A1 | 4/2015 |
| WO | 2015157446 A1 | 10/2015 |
| WO | 2016/109802 A1 | 7/2016 |

OTHER PUBLICATIONS

Tejwani et al., "Glycoengineering in CHO Cells: Advances in Systems Biology", Biotechnol. J. 13, 1700234 (1 of 16 pages), 2018 (Year: 2018).*
Patrick Dennler, et al., "Antibody Conjugates: From Heterogeneous Populations to Defined Reagents", Antibodies 2015, 4, 197-224; doi: 10.3390/antib4030197.
Puja Sapra, et al., "Investigational antibody drug conjugates for solid tumors", Expert Opinion 2011, 20, 1131-1149.
John A. Flygare, et al., "Antibody-Drug Conjugates for the Treatment of Cancer", Chem. Biol. Drugs Des. 2013; 81: 113-121.
Siler Panowski, et al., "Site-specific antibody drug conjugates for cancer therapy", MAbs 2013, 6, 34-45.
Joseph A. Francisco, et al., "cAC10-vcMMAE, an anti-CD30—monomethyl auristatin E conjugate with potent and selective antitumor activity", Blood 2003, 4, 1458-1465.
T. Shantha Raju, et al., "Galactosylation variations in marketed therapeutic antibodies", MAbs. 2012; 4(3): 385-391.
Natalie W. Nairn, et al., "Cysteine as a Monothiol Reducing Agent to Prevent Copper-Mediated Oxidation of Interferon Beta During PEGylation by CuAAC", Bioconjugate Chemistry 2015; 26(11): 2070-2075.
James D. Marks, et al., By-Passing Immunization: Building High Affinity Human Antibodies by Chain Shuffling, Bio/Technology 1992; 10: 779-783.
Nils Lonberg, et al., "Antigen-specific human antibodies from mice comprising four distinct genetic modifications", Nature 1994, vol. 368, pp. 859-391.
Sherie L. Morrison, "Success in specification", Nature 1994, vol. 368, pp. 812-813.
Dianne M. Fishwild, et al., "High-avidity human IgGk monoclonal antibodies from a novel strain of minilocus transgenic mice", Nature Biotechnology 1996, vol. 14, pp. 845-851.

(Continued)

*Primary Examiner* — Anand U Desai
(74) *Attorney, Agent, or Firm* — Ladas & Parry LLP

(57) ABSTRACT

A process for modifying glycoproteins is provided. The invention also provides a process for producing glycoprotein-payload conjugates, as well as the conjugates produced thereby.

36 Claims, 37 Drawing Sheets

(56) References Cited

OTHER PUBLICATIONS

Michael Neuberger, "Generating high-avidity human Mabs in mice", Nature Biotechnology 1996, vol. 14, pp. 826-827.
Nils Lonberg, et al., "Human Antibodies from Transgenic Mice", Intern. Rev. Immunol. 1995, vol. 13, pp. 65-93.
Florentina Kubizek, et al., "Status Quo in Antibody-Drug Conjugates—Can Glyco-Enzymes Solve the Current Challenges?", Bentham Science 2017, vol. 24, pp. 686-695.
Richard A. Evans, "The Rise of Azide-Alkyne 1,3-Dipolar 'Click' Cycloaddition and its Application to Polymer Science and Surface Modification", Australian Journal of Chemistry 2007, vol. 60, No. 6, pp. 384-395.
Emma M. Dangerfield, et al., "Protecting-Group-Free Synthesis of Amines: Synthesis of Primary Amines from Aldehydes via Reductive Amination", J. Org. Chem. 2010, vol. 75, pp. 5470-5477.
Mahmood Tajbakhsh, et al., "Catalyst-Free One-Pot Reductive Alkylation of Primary and Secondary Amines and N,N-Dimethylation of Amino Acids Using Sodium Borohydride in 2,2,2-Trifluoroethanol", Synthesis 2011, No. 3, pp. 490-496.
Paresh Agarwal, et al., "Hydrazino-Pictet-Spengler Ligation as a Biocompatible Method for the Generation of Stable Protein Conjugates", Bioconjugate Chemistry 2013, vol. 24, No. 6, pp. 846-851.
Feng Tang, et al., "One-pot N-glycosylation remodeling of IgG with non-natural sialylglycopeptides enables glycosite-specific and dual-payload antibody-drug conjugates†", Organic & Biomolecular Chemistry, Oct. 12, 2013, vol. 14, No. 40, pp. 9501-9518.
Elizabeth L. Smith, et al., "Chemoenzymatic Fc Glycosylation via Engineered Aldehyde Tags", Bioconjugate Chemistry Apr. 16, 2014, vol. 25, No. 4, pp. 788-795.
Thomas B. Parsons, et al., "Optimal Synthetic Glycosylation of a Therapeutic Antibody", Angew. Chem. Int. Ed. Engl. Feb. 12, 2016, vol. 55, No. 7, pp. 2361-2367.
Remon van Geel, et al., "Chemoenzymatic Conjugation of Toxic Payloads to the Globally Conserved N-Glycan of Native mAbs Provides Homogeneous and Highly Efficacious Antibody-Drug Conjugates", Bioconjugate Chem. 2015, vol. 26, pp. 2235-2242.
Saroja Narasimhan, "Control of Glycoprotein Synthesis", The Journal of Biological Chemistry, Sep. 10, 1982, vol. 257, No. 17, pp. 10235-10242.
Hartmuth C. Kolb, et al., "Click Chemistry: Diverse Chemical Function from a Few Good Reactions", Anwe. Chem Int. Ed. 2001, vol. 40, pp. 2004-2021.
International Search Report of the corresponding PCT application No. PCT/US17/68872.
Written Opinion of the corresponding PCT application No. PCT/US17/68872.
Remon Van Geel et al.; "Chemoenzymatic Conjugation of Toxic Payloads to the Globally Conserved N-Glycan of Native mAbs Provides Homogeneous and Highly Efficacious Antibody-Drug Conjugates"; Bioconjugate Chem. 2015; vol. 26; pp. 2233-2242: entire document, especially: p. 2233; col. 2; para. 2 to p. 2234; col 1; para 1; p. 2234; col. 1, para 3; p. 2235, col. 1, para 1; p. 2235, col. 1, para 2; Figure 1A; Figure 1B.
Saroja Narasimhan; "Control of Glycoprotein Synthesis"; The Journal of Biological 1-32 Chemistry. 1982. vol. 257(17), pp. 10235-10242, Entire Document.
Extended European Search Report in application EP 17889215.4, dated Aug. 5, 2020.
Office Action issued by the Japanese Patent Office dated Aug. 25, 2020 for counterpart counterpart application. No. JP 2019-534823 and an English translation.
Office Action issued by the Korean Patent Office dated Dec. 16, 2020 for counterpart counterpart application. KR No. 10-2019-7019261 and an English translation.

\* cited by examiner

PROCESSES FOR PREPARING GLYCOPROTEIN-DRUG CONJUGATES

CROSS REFERENCE

This application is a national phase entry under 35 USC 371 of International Patent Application No.: PCT/US2017/068872 filed on 29 Dec. 2017. This application claims the benefit of U.S. Provisional Patent Application No. 62/440,075, filed on 29 Dec. 2016, the entire content of which is incorporated by reference.

FIELD OF THE INVENTION

The present invention relates to a method for modifying glycoproteins so that the glycoproteins comprise one or more tri-mannosyl cores. The present invention also relates to glycoprotein-payload conjugates, which comprise the glycoprotein of the invention and a payload of interest.

BACKGROUND OF INVENTION

Therapeutic protein drugs have been widely used in clinic, and due to their advantages of high value, high specificity and low toxicities, some of big pharmaceutical companies in the world devote themselves in the development of this category of drugs to clinical trials. Most of these therapeutic proteins are monoclonal antibodies. Even though some of patients are satisfied with their clinical outcomes, the clinical trial data suggest that the therapeutic effects of some of these antibodies still need to be improved, particularly, in cancer treatments. To solve this disadvantage, scientists start to focus on modifying these clinical antibodies so as to improve their efficacies in the cancer therapy by some technologies. Among these technologies, antibody-drug conjugates (ADCs) draw more attentions due to their chemistry, manufacturing and control (CMC) friendly, user friendly, and lower side effects. So far, there are 4 therapeutic antibody-drug conjugates available in the market, including Mylotarg®, Adcetris®, Besponsa® and Kadcyla®; many are others are under development (Kubizek F1, Eggenreich B1, Spadiut O1. Protein Pept Lett. 2017, 24(8):686-695; Fischer E., Roger Schibli R. Antibodies 2015, 4, 197-224; Sapra, P., Hooper, A., O'Donnell, C. and Gerber, H.-P. Expert Opin. Investig. Drugs 2011, 20, 1131-1180; Flygare, J., Pillow, T. and Aristoff, P., Chem. Biol. Drug Des. 2013, 81, 113-121; Panowski, S.; Bhakta, S.; Raab, H.; Polakis, P. and Junutula, J. R. Site-specific antibody drug conjugates for cancer therapy. MAbs 2013, 6, 34-45).

In these clinical ADCs, Kadcyla and Mylotarg are formed by randomly conjugating a payload or linker to amine groups of lysine residues, however, Adcetris®, brentuximab vedotin (cAC10-vcMMAE, SGN-35), is a chimeric anti-CD30 monoclonal antibody with the fusion of the variable heavy and light region of the murine anti-CD30 antibody AC10. An average of 4 (2-8) MMAE molecules are conjugated to the SGN-30 scaffold. The conjugated points of MMAE are random SH groups of cysteine residues produced by mild reduction of the inter-chain disulfide bonds. The linker consists of a thiol-reactive maleimidocaproyl spacer, the dipeptide valinecitrulline linker, and a PABC spacer (Francisco J A, Cerveny C G, Meyer D L, Mixan B J, Klussman K, Chace D F, Rejniak S X et al. cAC10-vcMMAE. Blood 2003, 4, 1458-65). Although such technologies easily conjugate a payload or linker to an antibody, due to the problems of the multiple lysine sequences and the optimal reaction of reduction cysteine residues in an antibody, it is difficult for these two technologies to control the drug-to-antibody ratio (DAR) of the conjugates. These phenomena always cause the heterogeneity of antibody products and induce CMC problems. Some literatures even indicate that this type of first generation non site-specific ADC has disadvantages of PK and immunogenicity.

To solve these disadvantages of first generation ADC, site-specific ADC platforms are developed including SMART-Tag, non-nature amino acid any tyrosine, therapeutic sortase, Thio-Bridge, etc. As we expect, these technologies are capable of generating homogeneous ADC products by engineering some specific sites or domains in parent antibodies. For example the Thio-Bridge technology connects the linker and the payload to the partially reduced disulfide bonds of antibodies. The SMART-Tag is a technology by mutating the adjacent sequence of an antibody as a substrate sequence of bacteria oxidase. The resulting product with formaldehydes is used as the connect site of linker and payload. As expected these second generation ADC technologies are able to generate ADC products with unique DARs and high homogeneity. However, due to the mutation of nature antibodies, the ADC products may have PK and immunogenicity problems. Presently, the conjugation of a payload to an antibody through N-glycosylation is drawn a lot of attentions due to the successful development of glycolengineering of antibodies.

All naturally occurring IgGs and recombinant antibodies have an amino acid asparagine at position 297 (Asn297) in each of the heavy chain $CH_2$ constant regions which is an N-glycosylation site. By the glycosylation and post modification in mammalian cells, two di-antenna-shaped glycan moieties are formed through the N-glycosylation on an IgG, and each of the di-antenna-shaped glycan moieties is basically constructed by at least 7 sugar moieties having the following formula:

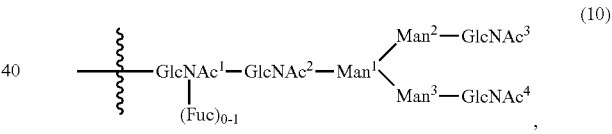

(10)

in which a first GlcNAc ($GlcNAc^1$) respectively bonds to Asn297 of the antibody and a second GlcNAc ($GlcNAc^2$), and optionally a fucose sugar (Fuc); $GlcNAc^2$ further bonds to a first mannose (Mau1); a second and a third mannose ($Man^2$ and $Man^3$) respectively bond to the α-1,3 and α-1,6 positions of $Man^1$; and two further GlcNAc sugars ($GlcNAc^3$ and $GlcNAc^4$) respectively bond to the β-1,2 positions of $Man^2$ and $Man^3$. An antibody having such glycan moieties with Fucose represented as G0F, however, when the fucose moiety is absent, the antibody is G0. (T. Shantha Raju MAbs. 2012 May 1; 4(3): 385-391). When either $GlcNAc^3$ or $GlcNAc^4$ bonds to an additional galacytose sugar, the antibody is represented as G1F/G1 antibody. When both the terminal GlcNAc sugars in the glycan moiety of an antibody respectively bond to two additional galacytose sugars, the antibody is represented as G2F/G2 antibody. Antibodies produced by mammalian cells generally may include G0F (more than about 40%), G1F (about 30%-40%) and G2F (less than 1%), and a very small amount of G1F/G1 and G2F/G2 linking to sialic acid.

Because engineering each branching site in the N297 glycans maintains the structure intact and creates some functional diversity, for example ADCC, half life and CDC, of antibodies, some N297 glycoengineering ADC platforms have been developed and some of products are in the clinical trial stage. WO 2014/164534 A2, WO 2014/065661 A1, WO 2015/032899 A1, WO 2015/057064 A1, WO 2015/157446 A1, U.S. Pat. No. 8,716,033 B2, U.S. Pat. No. 7,416,858 B2, EP 2753752 B3 and a review article (Bioconjug Chem.; 2015 Nov. 18; 26(11):2070-5) have disclosed many modified glycan moieties for antibody drug conjugations. However, the drug antibody ratios (DAR) in an antibody-drug conjugation cannot be well controlled and the payload diversity cannot be performed in these technologies, and thus there is a need in the art for controlling the drug antibody ratio and increasing payload diversity of an ADC. The invention fulfills that need and provides other benefits.

SUMMARY OF INVENTION

One aspect of the invention provides a process for producing a glycoprotein-payload conjugate comprising a structure of formula (1):

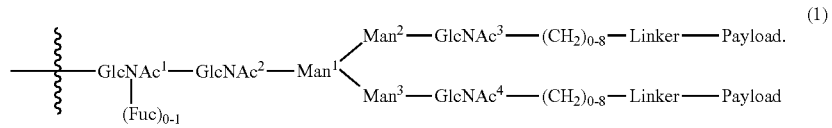

(1)

Another aspect of the invention provides a process for producing a glycoprotein-payload conjugate comprising a structure of formula (5):

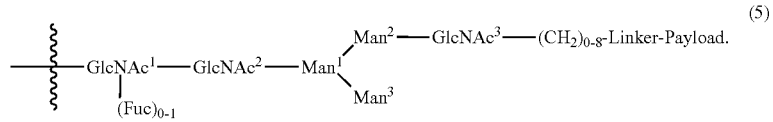

(5)

Another aspect of the invention provides a process for producing a glycoprotein-payload AB conjugate comprising a structure of formula (7)

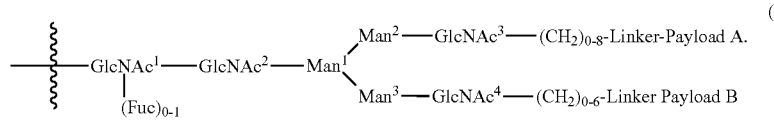

(7)

Another aspect of the invention provides glycoprotein-payload conjugates obtainable by the processes of the invention.

DETAILED DESCRIPTION OF THE INVENTION

Figure 1:
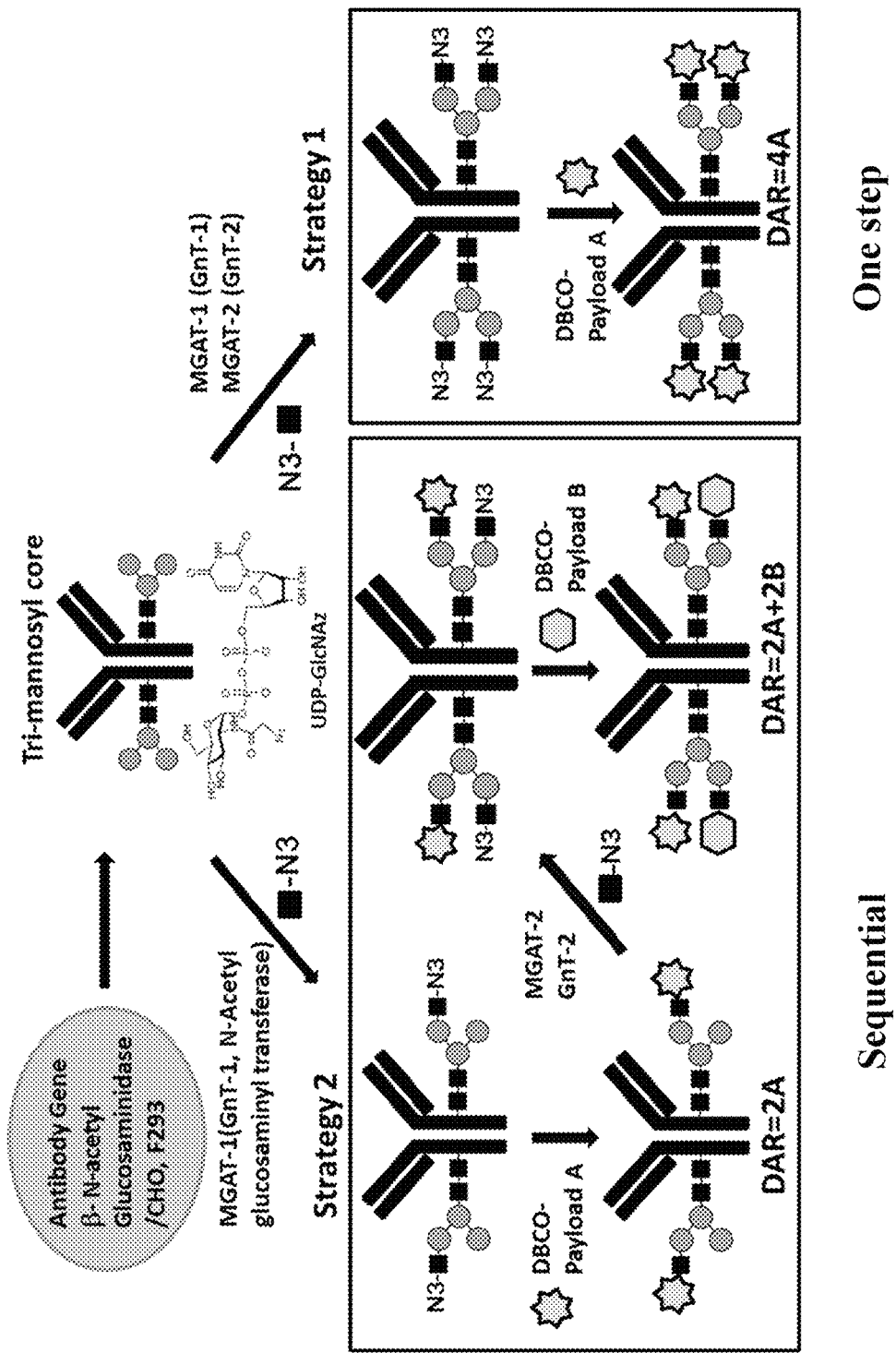
FIG. 1 shows one-step and sequential strategies for producing tri-mannosyl antibody drug conjugates.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art.

Abbreviations
ADC antibody-drug conjugate
DAR drug-to-antibody ratio
Asn asparagine
GlcNAc N-acetylglucosamine
GlcNAz N-azidoacetylglucosamine
Fuc fucose
Man mannose
MGAT-1; GnT-1 mannosyl (α-1,3-)-glycoprotein β-1,2-N-acetylglucosaminyltransferase
MGAT-2; GnT-2 mannosyl (α-1,6-)-glycoprotein β-1,2-N-acetylglucosaminyltransferase
UDP uridine diphosphate
DBCO dibenzocyclooctyne group
DM1 mertansine
PEG polyethylene glyco
MES 4-morpholineethanesulfonic acid
MMAE monomethyl auristatin E
MMAF monomethyl auristatin F
TMCC3 transmembrane and coiled-coil domain family 3

It should be noted that as used herein and in the appended claims, the singular forms "a," "an," and "the" include plural reference unless the context clearly dictates otherwise. As well, the terms "a" (or "an"), "one or more" and "at least one" can be used interchangeably herein. It is also to be noted that the terms "comprising," "including," and "having" can be used interchangeably.

Often, ranges are expressed herein as from "about" one particular value and/or to "about" another particular value. When such a range is expressed, an embodiment includes the range from the one particular value and/or to the other particular value. Similarly, when values are expressed as approximations, by use of the word "about," it will be understood that the particular value forms another embodiment. It will be further understood that the endpoints of each of the ranges are significant both in relation to and independently of the other endpoint. As used herein the term "about" refers to ±20%, ±15%, ±10%, ±9%, ±8%, ±7%, ±6%, ±5%, ±4%, ±3%, ±2%, ±1%, ±0.5%, or ±0.25%.

When referring to a formulation component, it is intended that the term used, e.g., "agent," encompass not only the specified molecular entity but also its pharmaceutically acceptable analogs, including, but not limited to, salts, esters, amides, prodrugs, conjugates, active metabolites, and other such derivatives, analogs, and related compounds.

The general term "sugar" used herein indicates a monosaccharide, for example glucose (Glc), galactose (Gal), mannose (Man) and fucose (Fuc), as well as derivatives of a monosaccharide, such as an amino sugar and a sugar acid, e.g., glucosamine (GlcN), galactosamine (Gain), N-acetyl-glucosamine (GlcNAc), N-azidoacetylglucosamine (GlcNAZ), N-acetylgalactosamine (GlaNAc), N-acetyl-neuraminic acid (NeuNAc), N-acetlymuramic acid (Mur-NAc), glucuronic acid (GlcA), and iduronic acid (IdoA).

As used herein, the term "protein" can include a polypeptide having a native amino acid sequence, as well as variants and modified forms regardless of their origin or mode of preparation. A protein which has a native amino acid sequence is a protein having the same amino acid sequence as obtained from nature. Such native sequence proteins can be isolated from nature or can be prepared using standard recombinant and/or synthetic methods. Native sequence proteins specifically encompass naturally occurring truncated or soluble forms, naturally occurring variant forms (e.g., alternatively spliced forms), naturally occurring allelic variants and forms including post-translational modifications. A native sequence protein includes proteins following post-translational modifications such as glycosylation, or phosphorylation, or other modifications of some amino acid residues.

As used herein, the term "glycoprotein" refers to a protein comprising one or more monosaccharide or oligosaccharide chains covalently bonded to the protein. A glycan may be attached to a hydroxyl group of the protein (O-linked-glycosyl), e.g., to the hydroxy group of serine, threonine, tyrosine, hydroxylysine or hydroxyproline, or to an amide on the protein (N-glycoprotein), e.g., asparagine or arginine, or to a carbon on the protein (C-glycoprotein), e.g., tryptophan. A glycoprotein may comprise more than one glycan, may comprise a combination of one or more monosaccharide and one or more oligosaccharide glycans, and may comprise a combination of N-linked, O-linked and C-linked glycans. Examples of glycoproteins include ligands specific to surface antigens of cells, prostate-specific membrane antigen, *Candida antarctica* lipase, gp41, gp120, erythropoietin (EPO), antifreeze protein and antibodies.

An antibody is a protein generated by the immune system that is capable of recognizing and binding to a specific antigen. The term antibody herein is used in its broadest sense and specifically includes monoclonal antibodies, polyclonal antibodies, dimers, multimers, multispecific antibodies (e.g. bispecific antibodies), antibody fragments, and double and single chain antibodies. The term "antibody" is herein also meant to include human antibodies, humanized antibodies, chimeric antibodies and antibodies specifically binding cancer antigen. The term "antibody" is meant to include whole antibodies, but also fragments of an antibody, for example an antibody Fab fragment, F(ab)2, Fv fragment or Fc fragment from a cleaved antibody, an scFv-Fc fragment, a minibody, a diabody or an scFv. Furthermore, the term includes genetically engineered derivatives of an antibody. Antibodies, fragments of antibodies and genetically engineered antibodies may be obtained by methods that are known in the art. Suitable marketed antibodies include, but are not limited to, abciximab, rituximab, basiliximab, palivizumab, infliximab, trastuzumab, alemtuzumab, adalimumab, tositumomab-1131, cetuximab, ibrituximab tiuxetan, omalizumab, bevacizumab, natalizumab, ranibizumab, panitumumab, eculizumab, certolizumab pegol, golimumab, canakinumab, cattunaxomab, ustelcinurnab, tocilizumab, ofatumumab, denostunab, belimumab, ipilimumab and brentuximab.

Antibodies can be produced using any number of expression systems, including prokaryotic and eukaryotic expression systems. In some embodiments, the expression system is a mammalian cell expression, such as a hybridoma, or a CHO cell expression system. Many such systems are widely available from commercial suppliers. In embodiments in which an antibody comprises both a $V_H$ and $V_L$ region, the $V_H$ and $V_L$ regions may be expressed using a single vector, e.g., in a di-cistronic expression unit, or under the control of different promoters. In other embodiments, the $V_H$ and $V_L$ region may be expressed using separate vectors. A $V_H$ or $V_L$ region as described herein may optionally comprise a methionine at the N-terminus.

The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity.

Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, can be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)).

As used herein, "GlcNAc$^1$," "GlcNAc$^2$," "GlcNAc$^3$," and "GlcNAc$^4$" respectively represent the GlcNAc sugars at different positions of an antenna-shaped glycan moiety.

As used herein,

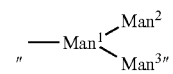

represents a tri-mannosyl structure comprising three mannoses, wherein the first mannose (Man$^1$) links to a GlcNAc sugar; and the second and third mannoses (Man$^2$ and Man$^1$) respectively link to Man$^1$ through α-1,3 and α-1,6 glycosidic linkages.

As used herein, "-(Fuc)$_{0-1}$" represents that a fucose sugar is optionally existing, and when present, there is only one fucose sugar.

As used herein, "—(CH$_2$)$_{0-8}$—" represents that —CH$_2$— may or may not exist, and when present, it may independently be 1, 2, 3, 4, 5, 6, 7 or 8 —CH$_2$— groups.

One aspect of the invention provides a process for producing a glycoprotein-payload conjugate comprising a structure of formula (1):

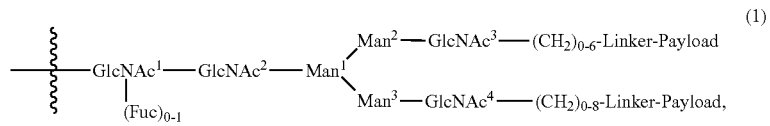

(1)

which comprises the steps of:

(i) reacting a glycoprotein comprising a glycan having formula (2)

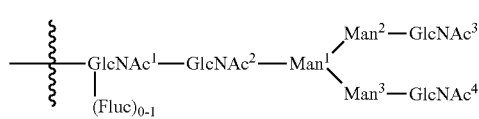

(2)

with β-N-acetylglucosaminidase to produce a modified glycoprotein comprising a tri-mannosyl core of formula (3)

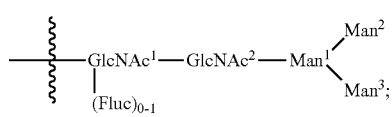

(3)

(ii) reacting the modified glycoprotein comprising the tri-mannosyl core of formula (3) with UDP-GlcNAc-(CH$_2$)$_{0-8}$—R, wherein R is azido, a ketone group or an aldehyde, in the presence of mannosyl (α-1,3-)-glycoprotein β-1,2-N-acetylglucosaminyltransferase and mannosyl (α-1,6-)-glycoprotein β-1,2-N-acetylglucosannnyltransferase to allow two GlcNAc-(CH$_2$)$_{0-8}$—R sugars to respectively bond to β-1,2 position of each of Man$^2$ and Man$^3$, and whereby a glycan moiety of formula (4)

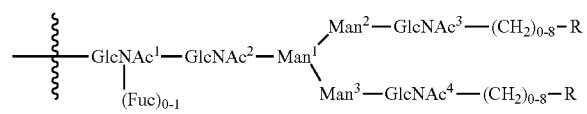

(4)

is formed; and (iii) reacting two conjugator-linker-payloads, wherein the payloads of the two conjugator-linker-payloads are the same or different, with the glycan moiety of formula (4) to produce the glycoprotein-payload conjugate comprising the structure of formula (1).

In some embodiments, the two payloads are different, the payloads can be attached to any of the four Man-GlcNAc structures in the glycoprotein in a random manner.

Another aspect of the invention provides a process for producing a glycoprotein-payload conjugate comprising a structure of formula (5):

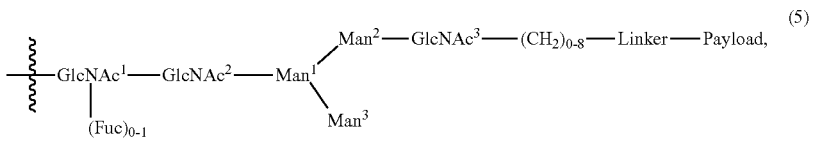

(5)

which comprises the steps of:

(i) reacting a modified glycoprotein comprising a tri-mannosyl core of formula (3) defined above with UDP-GlcNAc-(CH$_2$)$_{0-8}$—R, wherein R is azido, a ketone group or an aldehyde, in the presence of mannosyl (α-1,3-)-glycoprotein β-1,2-N-acetylglucosaminyltransferase to allow the GlcNAc-(CH$_2$)$_{0-8}$—R sugar to bond to β-1,2 position of Man$^2$, and whereby a glycoprotein comprising a glycan moiety of formula (6)

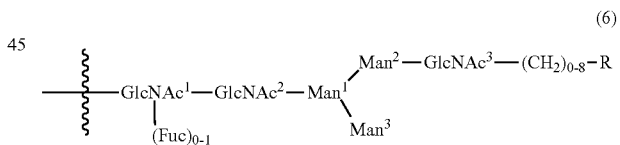

(6)

is formed; and (ii) reacting a conjugator-linker-payload with the glycoprotein comprising the glycan moiety of formula (6) to produce the glycoprotein-payload conjugate comprising the structure of formula (5).

In some embodiments, in order to precisely control the positions of the payloads attached, a glycoprotein-payload AB conjugate comprising a structure of formula (7)

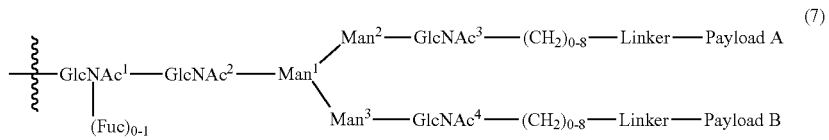

(7)

can be produced by the following steps:

(i) reacting the modified glycoprotein comprising the tri-mannosyl core of formula (3) defined above with UDP-GlcNAc-$(CH_2)_{0-8}$—R, wherein R is azido, a ketone group or an aldehyde, in the presence of mannosyl ($\alpha$-1,3-)-glycoprotein $\beta$-1,2-N-acetylglucosaminyltransferase to allow the GlcNAc-$(CH_2)_{0-8}$—R sugar to bond to $\beta$-1,2 position of $Man^2$, and whereby a glycoprotein comprising a glycan moiety of formula (6) defined above is formed;

(ii) reacting a conjugator-linker-payload A with the glycoprotein comprising the glycan moiety of formula (6) to produce a glycoprotein-payload A conjugate comprising the structure of formula (8)

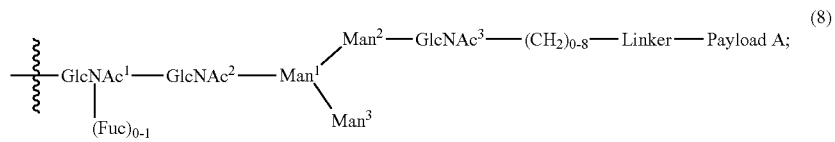

(iii) reacting the glycoprotein-payload A conjugate comprising the structure of formula (8) with UDP-GlcNAc-$(CH_2)_{0-8}$—R, wherein R is azido, a ketone group or an aldehyde, in the presence of mannosyl ($\alpha$-1,6-)-glycoprotein $\beta$-1,2-N-acetylglucosaminyltransferase to allow the GlcNAc-$(CH_2)_{0-8}$—R sugar to bond to $\beta$-1,2 position of $Man^3$, and whereby a glycoprotein comprising a glycan-payload A moiety having formula (9)

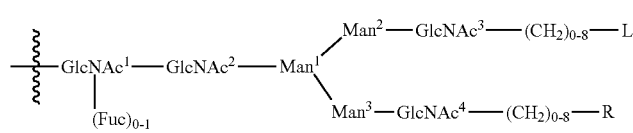

is formed; and (iv) reacting a conjugator-linker-payload B with the glycoprotein comprising the glycan-payload A moiety having formula (9) to produce to produce the glycoprotein-payload A/B conjugate comprising the structure of formula (7), wherein the payload A and the payload B are the same or different.

Glycoproteins as used herein may be obtained, for example, by solid-state peptide synthesis (e.g. Merrifield solid phase synthesis) or recombinant production. For recombinant production one or more polynucleotide encoding the glycoprotein is isolated and inserted into a vector for further cloning and/or expression in a host cell. Such polynucleotide may be readily isolated and sequenced using conventional procedures. Methods which are well known to those skilled in the art can be used to construct expression vectors containing the coding sequence of the glycoprotein. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y. (1989).

As used herein, β-N-etylglucosaminidase represents a glycosidase family that catalyzes the hydrolysis of β-N-Acetylglucosamine residues from oligosaccharides. Many β-N-Acetyl-glucosaminidases have been found to have board hydrolysis ability in catalyzing multiple types of β-glycosidic linkage. In a preferred embodiment, the β-N-acetylglucosaminidase may be an exoglycosidase which is capable of hydrolysizing beta 1-2 linkage located between terminal acetylglucosamine residues and N-glycan of a glycoprotein. Exo-β-N-acetylglucosaminidase variants can be obtained from different sources, such as *Streptococcus* spp. and *Canavalia enstformis.*

According to the invention, mannosyl (α-1,3-)-glycoprotein β-1,2-N-acetylglucosaminyltransferase (MGAT1; GnT-I; EC:2.4.1.101) transfers N-acetyl-D-glucosamine from UDP-GlcNAc to a terminal mannose which is linked to another sugar moiety or glycan through alpha 1-3 glycosidic linkage. The linkage of GlcNAc and alpha 3 mannose transferred by MGAT1 is a β1-2 glycosidic bond. It has been found that MGAT1 is universally expressed in eukaryote because it is an essential enzyme to hybrid and complex N-glycan biosynthesis in Golgi.

According to the invention, mannosyl (α-1,6-)-glycoprotein β-1,2-N-acetylglucosaminyltransferase (MGAT2; GnT-II; EC 2.4.1.143) transfers N-acetyl-D-glucosamine from UDP-GlcNAc to a terminal mannose which is linked to another sugar moiety or glycan through alpha 1-6 glycosidic linkage. The linkage of GlcNAc and alpha 6 mannose transferred by MGATII is beta 1-2 glycosidic bond. It has been found that MGAT2 is universally expressed in eukaryote because it is an essential enzyme for complex N-glycans biosynthesis in Golgi.

In some embodiments, the reaction between the glycoprotein comprising the glycan having formula (2) and β-N-acetylglucosaminidase is performed in a mammalian cell culture. In the mammalian cell culture, a mammalian cell line, which comprises a first polynucleotide encoding the glycoprotein comprising the glycan having formula (2), and a second polynucleotide encoding the β-N-acetylglucosaminidase, is incubated in a medium at a condition suitable for expression of the glycoprotein and the β-N-acetylglucosaminidase. Examples of mammalian host cell lines include monkey kidney CV1 line transformed by SV40 (COS-7); human embryonic kidney line (293 or 293T cells), baby hamster kidney cells (BHK), mouse sertoli cells (TM4 cells), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells, MRC 5 cells, FS4 cells, Chinese hamster ovary (CHO) cells, and myeloma cell lines such as YO, NS0, P3X63 and Sp2/0.

In some embodiments of the invention, the glycoprotein is an antibody or fragments thereof. The antibody or fragments thereof can be antibody Fab fragment, F(ab')2, Fv fragment or Fc fragment from a cleaved antibody, an scFv-Fc fragment, a minibody, a diabody or an scFv. In a preferred embodiment, the antibody is Herceptin, trastuzumab or an anti-TMCC3 antibody.

In an embodiment of the invention, when R is azido, and the conjugator is alkynyl, the conjugator-linker-payload reacts with -GlcNAc-$(CH_2)_{0-8}$—R group to form -GlcNAc-$(CH_2)_{0-8}$-linker-payload through click reaction (Angewandte Chemie International Edition. 40 (11): 2004-2021; and Australian Journal of Chemistry. 60 (6): 384-395). In another embodiment, when R is an a ketone group or an aldehyde, and the conjugator is amino, the conjugator-linker-payload reacts with -GlcNAc-$(CH_2)_{0-8}$—R grout to form -GlcNAc-$(CH_2)_{0-8}$-linker-payload through reductive amination (J. Org. Chem., 2010, 75, 5470-5477; and Synthesis, 2011, 490-496). In a further embodiment, when R is an a ketone group or an aldehyde, and the conjugator is β-arylethylamino, the conjugator-linker-payload reacts with the -GlcNAc-$(CH_2)_{0-8}$—R group to form -GlcNAc-$(CH_2)_{0-8}$-linker-payload through Pictet-Spengler reaction (Bioconjugate Chem., 2013, 24 (6), pp 846-851).

In some embodiments, when the glycoprotein-payload conjugate is used for treatment of a disease in a subject, the payload may be a therapeutic agent. The therapeutic agent can be a cytostatic or cytotoxic agent or an isotope-chelating agent with corresponding radioisotopes. Examples of the cytostatic or cytotoxic agent include, without limitation, antimetabolites (e.g., fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, gemcitabine, capecitibine, azathioprine, cytosine methotrexate, trimethoprim, pyrimethamine, or pemetrexed); alkylating agents (e.g., cmelphalan, chlorambucil, busulfan, thiotepa, ifosfamide, carmustine, lomustine, semustine, streptozocin, dacarbazine, mitomycin C, cyclophosphamide, mechlorethamine, uramustine, dibromomannitol, tetranitrate, procarbazine, altretamine, mitozolomide, or temozolomide); alkylating-like agents (e.g., cisplatin, carboplatin, nedaplatin, oxaliplatin, satraplatin, or triplatin); DNA minor groove alkylating agents (e.g., duocarmycins such as CC-1065, and any analogs or derivatives thereof; pyrrolobenzodiazapenes, or any analogs or derivatives thereof); anthracyclines (e.g., daunorubicin, doxorubicin, epirubicin, idarubicin, or valrubicin); antibiotics (e.g., dactinomycin, bleomycin, mithramycin, anthramycin, streptozotocin, gramicidin D, mitomycins (e.g., mitomycin C); calicheamicins; antimitotic agents (including, e.g., maytansinoids (such as DM1, DM3, and DM4), auristatins (including, e.g., monomethyl auristatin E (MMAE) and monomethyl auristatin F (MMAF)), dolastatins, cryptophycins, vinca alkaloids (e.g., vincristine, vinblastine, vindesine, vinorelbine), taxanes (e.g., paclitaxel, docetaxel, or a novel taxane), tubulysins, and colchicines); topoisomerase inhibitors (e.g., irinotecan, topotecan, camptothecin, etoposide, teniposide, amsacrine, or mitoxantrone); HDAC inhibitor (e.g., vorinostat, romidepsin, chidamide, panobinostat, or belinostat); proteasome inhibitors (e.g., peptidyl boronic acids); as well as radioisotopes such as $At^{211}$, $I^{131}$, $I^{125}$, $Y^{90}$, $Re^{186}$, $Re^{188}$, $Sm^{153}$, $Bi^{212}$ or $^{213}$, $P^{32}$ and radioactive iso topes of Lu including $Lu^{177}$. Examples of the isotope-chelating agents include, without limitation, ethylenediaminenetetraacetic acid (EDTA), diethylenetriamine-N,N,N',N''-pentaacetate (DTPA), 1,4,7,10-tetraazacyclododecane-N,N',N'',N'''-tetraacetate (DOTA), 1,4,7,10-tetrakis(2-hydroxypropyl)-1,4,7,10-tetraazacyclododecane (THP), triethylenetetramine-N,N,N',N'',N''',N'''-hexaacetate (TTHA), 1,4,7,10-tetraazacyclododecane-N,N',N'',N'''-tetrakis(methylenephosphonate) (DOTP), and mercaptoacetyltriglycine (MAG3).

In some embodiments, when the glycoprotein-payload conjugate is used for detection, the payload may be a label. The labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $P^{32}$, $C^{14}$, $I^{125}$, $H^3$, and $I^{131}$, fluorophores such as rare earth chelates or fluorescein and its derivatives, rhodamine and its derivatives, dansyl, umbelliferone, luceriferases, e.g., firefly luciferase and bacterial luciferase, luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like. In another embodiment, a label is a positron emitter. Positron emitters include but are not limited to $Ga^{68}$, $F^{18}$, $Cu^{64}$, $Y^{86}$, $Br^{76}$, $Zr^{89}$, and $I^{124}$.

In some embodiments, the linker has a functionality that is capable of reacting with an electrophilic group present on a glycoprotein. Examples of such electrophilic groups include, but are not limited to, aldehyde and ketone carbonyl groups. In some embodiments, a heteroatom of the reactive functionality of the linker can react with an electrophilic group on a glycoprotein and form a covalent bond to a glycoprotein unit. Nonlimiting examples of such reactive functionalities include, but are not limited to, hydrazide, oxime, amino, hydrazine, thiosemicarbazone, hydrazine carboxylate, and arylhydrazide.

In some embodiments, the conjugator has a functionality that is capable of reacting with an electrophilic group present on a glycoprotein. Examples of such electrophilic groups include, but are not limited to, azide, aldehyde and ketone groups. In some embodiments, a heteroatom of the reactive functionality of the conjugator can react with an electrophilic group on a glycoprotein and form a covalent bond to a glycoprotein unit. Nonlimiting examples of such reactive functionalities include, but are not limited to, alkyne, dibenzocyclooctyne, hydrazide, oxime, amino, hydrazine, thiosemicarbazone, hydrazine carboxylate, and arylhydrazide.

In some embodiments, the linker has a functionality that is capable of connecting conjugator and payload. Examples of such linkers include, but are not limited to, non-cleavable linkers and cleavable linkers. In some embodiments, non-cleavable linkers include, but are not limited to linear or branched alkyl, cycloalkyl, alkenyl, cycloalkenyl, alkynyl, aryl, heteroaryl, alkoxy, acyl, alkylamines, or arylamine group having 2 to 20 carbon atoms. In some embodiments, cleavable linkers include, but are not limited to disulfide containing linkers, acid labile linkers, photolabile linkers, peptidase labile linkers, and esterase labile linkers The following examples are presented to illustrate certain embodiments of the present invention, but should not be construed as limiting the scope of this invention. The scope of this invention includes a one step or a sequential process to generate a homogenous ADC with one species or dual species of payloads from a tri-mannosyl core antibody as shown in FIG. 1.

Figure 2:
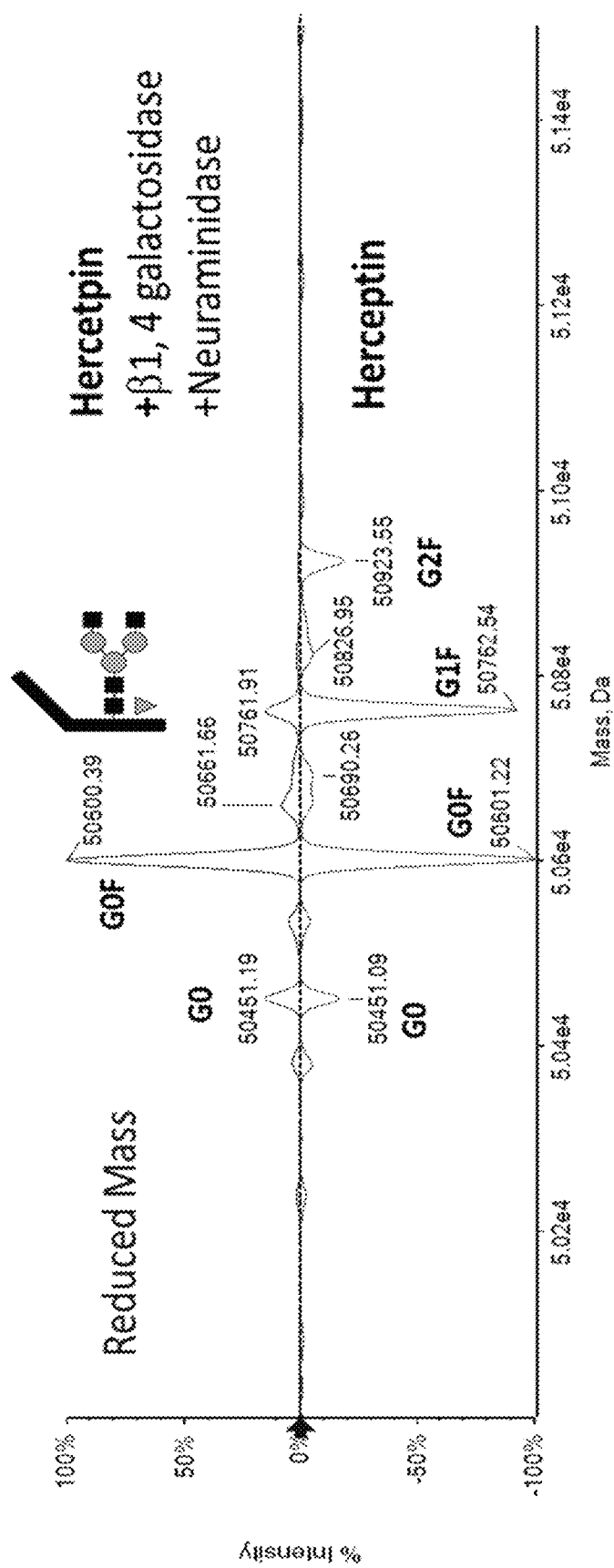
FIG. 2 shows the results of reduced mass chromatography analysis of Example 1. The results show that G0F/G0 type Herceptin was generated by the treatment of β1, 4 galactosidase and Neuraminidase.

Example 1. Preparation of Herceptin Antibody by Using β1,4-Galactosidase and Neuraminidase In order to remove glactose and sialic acid moieties of the N-glycan from Herceptin antibody (Roche Inc), 10 mg of Herceptin antibody was treated with 20 μl β1,4-Galactosidase (NEB, P0745L, 8 unit/μl) and 5 μl α2-3,6,8 neuraminidase (NEB, P0720L, 50 unit/μl) in 1× GlycoBuffer 1 (NEB, total volume 1 ml) at 37° C. for 24 hours. 10 μl of β1,4-Galactosidase (NEB, P0745L, 8 unit/μl) was further added to the reactant and the reaction was allowed to perform at 37° C. for further 24 hours to obtain a G0F/G0 antibody sample. The antibody sample was purified by using rProtein A Sepharose Fast Flow (GE Healthcare, 17-1279-02). After purification, the antibody sample was subjected to reduced mass chromatography analysis. The results shown in FIG. 2 reveal that the major amount of the antibodies in the sample is G0F (having a heavy chain with a molecular weight of 50,600 Da) and only a small amount is G0 (without a fucose sugar; having a heavy chain with a molecular weight of 50,451 Da).

Figure 3:
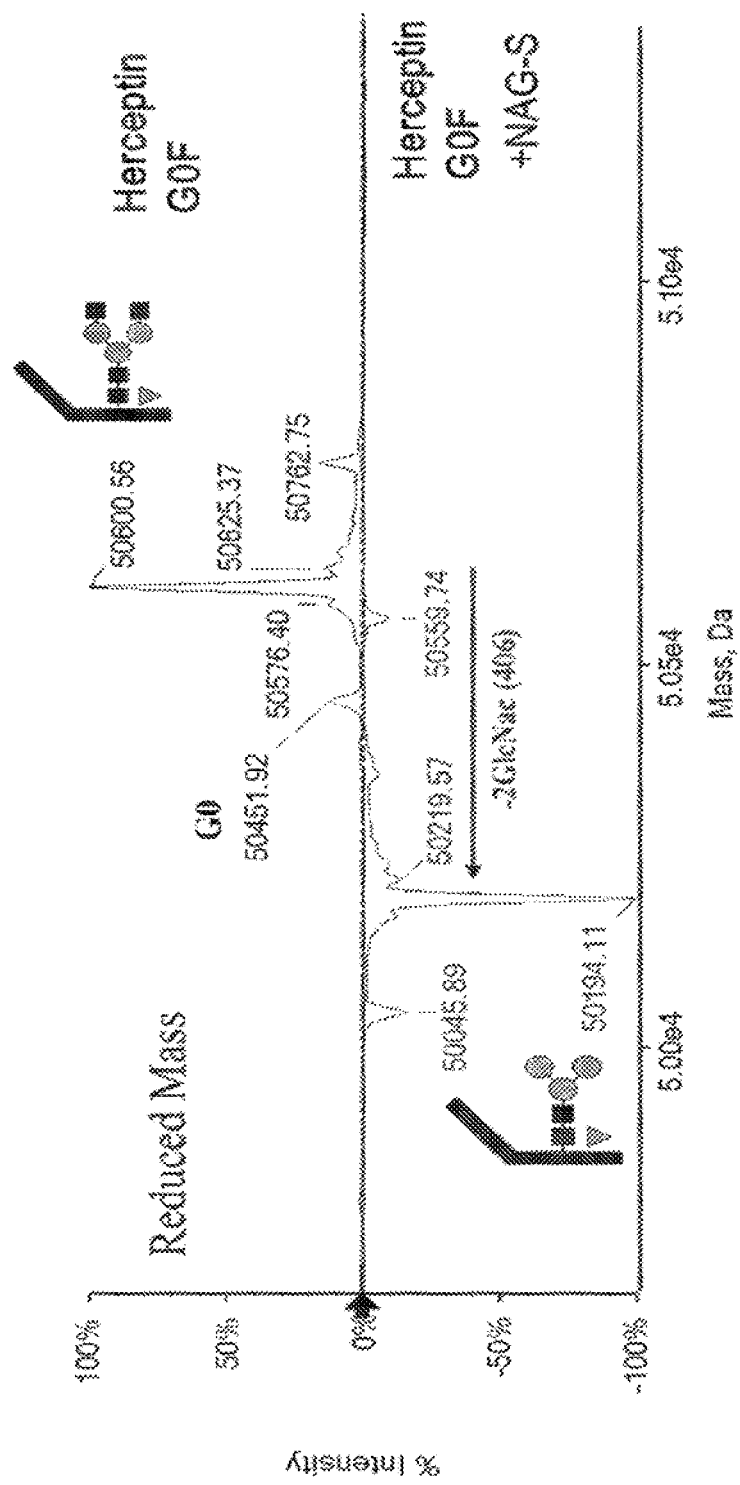
FIG. 3 shows the results of reduced mass chromatography analysis of Example 2. The results show that G0F/G0 type Herceptin was converted to tri-mannosyl core antibody by N-acetylglucosaminidase S.

Example 2. Conversion of Herceptin to Tri-Mannosyl Core Antibody 10 mg of G0F/G0 Hercepin antibody from Example 1 was treated with 20 μl β-N-Acetylglucosaminidase S (NEB, P0744L, 4 unit/μl) in 1× GlycoBuffer 1 (NEB, total volume 1 ml) at 37° C. for 24 hours. 10 μl of β-N-Acetylglucosaminidase S (NEB, P0744L, 4 unit/μl) was added to the reactant and the reaction was allowed to proceed at 37° C. for further 24 hours to obtain a digested antibody sample. The digested antibody sample was purified by using rProtein A Sepharose Fast Flow (GE Healthcare, 17-1279-02). After purification, the antibody sample was subjected to reduced mass chromatography analysis. The results shown in FIG. 3 reveal that a tri-mannosyl core Herceptin antibody having a heavy chain with a molecular weight of 50,194 Da was obtained and that almost all of G0F and G0 Hercetin antibodies were converted to tri-mannosyl core antibodies. It suggests that β-N-Acetylglucosaminidase S is capable of converting G0F and G0 antibodies to ones having tri-mannosyl Core at a high efficiency.

Example 3. Conjugation of GlcNAc to α-3 Mannose in One Arm of Each Heavy Chain of Tri-Mannosyl Core Herceptin Antibody by Mannosyl (α-1,3-)-Glycoprotein β-1,2-N-Acetylglucosaminyltransferase (MGAT-1; GnT-1)

Figure 4:
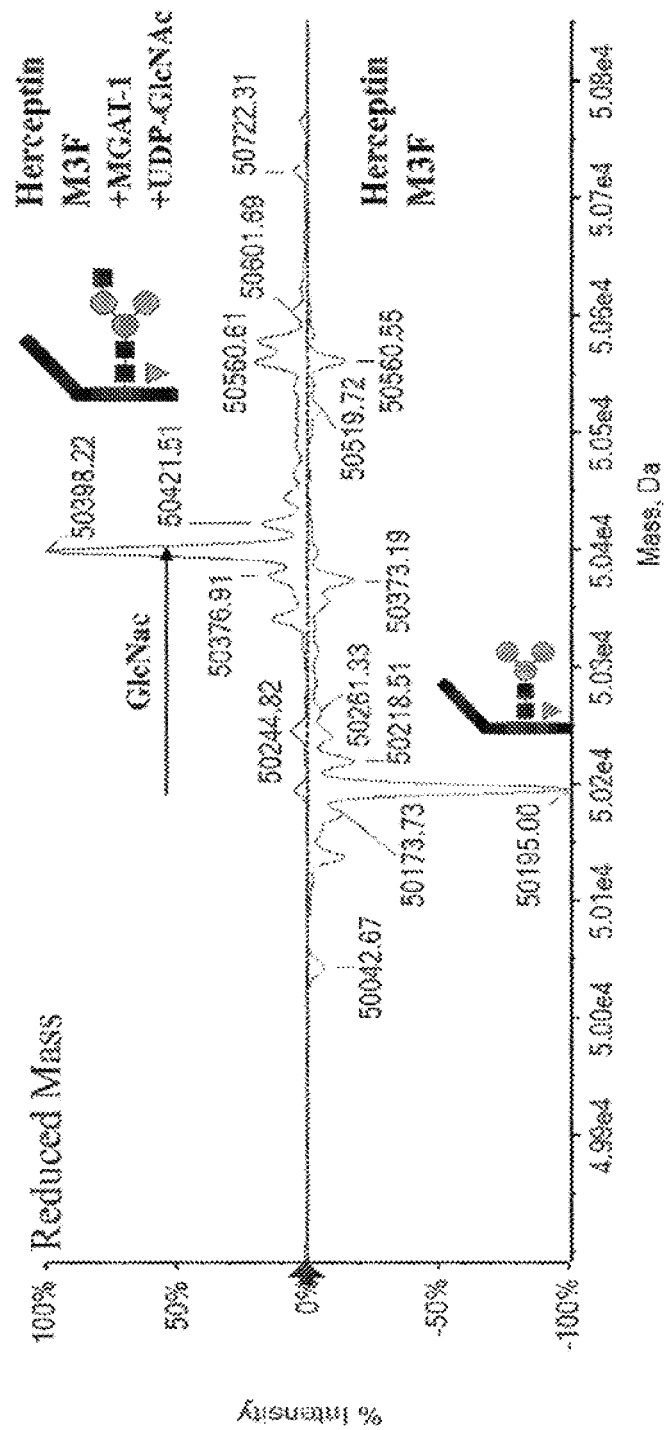
FIG. 4 shows the results of reduced mass chromatography analysis of Example 3. The results show that GlcNAC was conjugated to one arm of terminal mannose on each site of tri-mannosyl Herceptin by MGAT-1.

Tri-mannosyl core Herceptin antibody (40 μg) from Example 2 and UDP-GlcNAc (final concentration of 2.5 mM) (Sigma, U4375) in 80 μl 1× buffer SP (25 mM MES (4-morpholineethanesulfonic acid), 10 mM MnCl₂, pH 6.5) were incubated in the presence of MGAT-1 (0.15 μg; R&D, 8334-GT) at 37° C. for 16 hours. The product was subjected to a Reduced Mass Chromatography analysis. As the results shown in the FIG. 4, compared to tri-mannosyl core Herceptin antibody having a heavy chain with a molecular weight of 50,195 Da, an antibody product, whose heavy chain contains one more GlcNAc (molecular weight of 203 Da) and has a molecular weight of 50,398 Da, was obtained. It supports that MGAT-1 transfers only one N-acetylglucosamine to its substrate protein.

Example 4. Converting Tri-Mannosyl Core Herceptin Antibody to G0F/G0 Herceptin by MGAT-1 and Mannosyl (α-1,6-)-Glycoprotein β-1,2-N-Acetylglucosaminyltransferase (MGAT-2; GnT-2)

Figure 5:
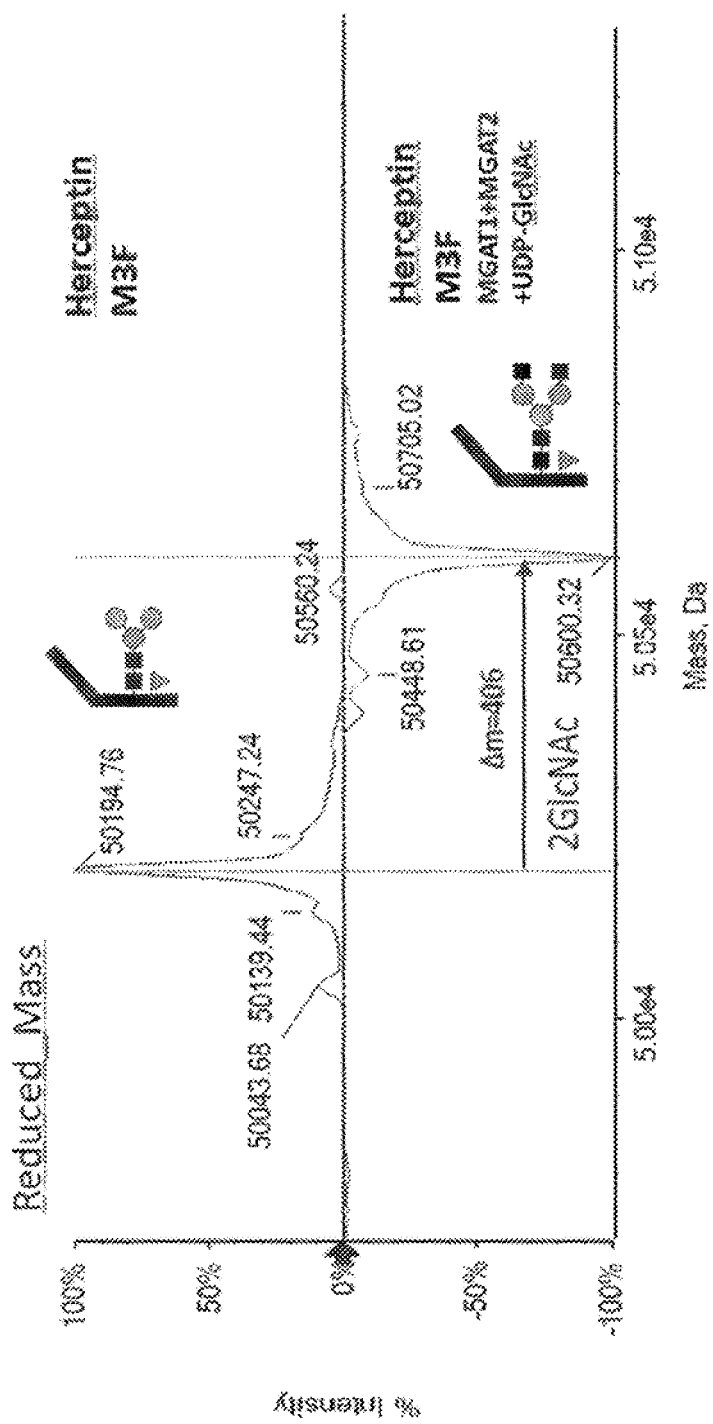
FIG. 5 shows the results of reduced mass chromatography analysis of Example 4. The results show that tri-mannosyl Herceptin was converted to a type G0/G0F Herceptin by MGAT-2 and MGAT-1.

Tri-mannosyl core Herceptin antibody (40 μg) from Example 2 and UDP-GlcNAc (final concentration of 2.5 mM) (Sigma, U4375) in 80 μl 1× buffer SP (25 mM MES, 10 mM MnCl₂, pH 6.5) were incubated in the presence of MGAT-1 (0.15 μg) and MGAT-2 (0.1 μg) at 37° C. for 16 hours. After the incubation, the reaction product was subjected to a reduced mass chromatography analysis. As the results shown in the FIG. 5, compared to tri-mannosyl core Herceptin antibody having a heavy chain with a molecular weight of 50,194 Da, an G0P antibody product with small amount of G0, whose heavy chain contains two more GlcNAcs (molecular weight of 203 Da×2) and has a molecular weight of 50,600 Da with, was obtained. These results indicate that by combining MGAT-1, MGAT-2 and N-acetylglucosamine, a tri-mannosyl core antibody can be transformed to a G0/G0F one.

Example 5. Tri-Mannosyl Core Herceptin Antibody is not a Substrate of MGAT-2

MGAT-2 transfers a GlcNAc sugar from UDP-GlcNAc to α(1,6) mannose of the tri-mannosyl core only when the tri-mannosyl core already has a GlcNAc sugar linked to α(1,3) mannose. In other words, if no GlcNAc sugar is linked to α(1,3) mannose of the tri-mannosyl core, MGAT-2 will be unable to transfer a GlcNAc sugar to either α(1,3) mannose or α(1,6) mannose. To confirm the above observation, tri-mannosyl core Herceptin antibody (40 μg) from Example 2 and UDP-GlcNAc (2.5 mM) in 80 μl 1× buffer SP (25 mM MES, 10 mM MnCl₂, pH 6.5) were incubated in the presence of MGAT-2 (0.1 at 37° C. for 16 hours. The product was subjected to a reduced mass chromatography analysis. There is no significant change to molecular weight of the tri-mannosyl core antibody in the mass spectrum (data not shown). This result suggests that the tri-mannosyl core is not a substrate of MGAT-2, and that MGAT-2 needs the conversion product of MGAT-1 to generate a G0F/G0 type antibody.

Example 6. Conjugation of GlcNAz to Terminal α-3 Mannose of One Arm of Each Heavy Chain of Tri-Mannosyl Core Herceptin Antibody by MGAT-1

Figure 6:
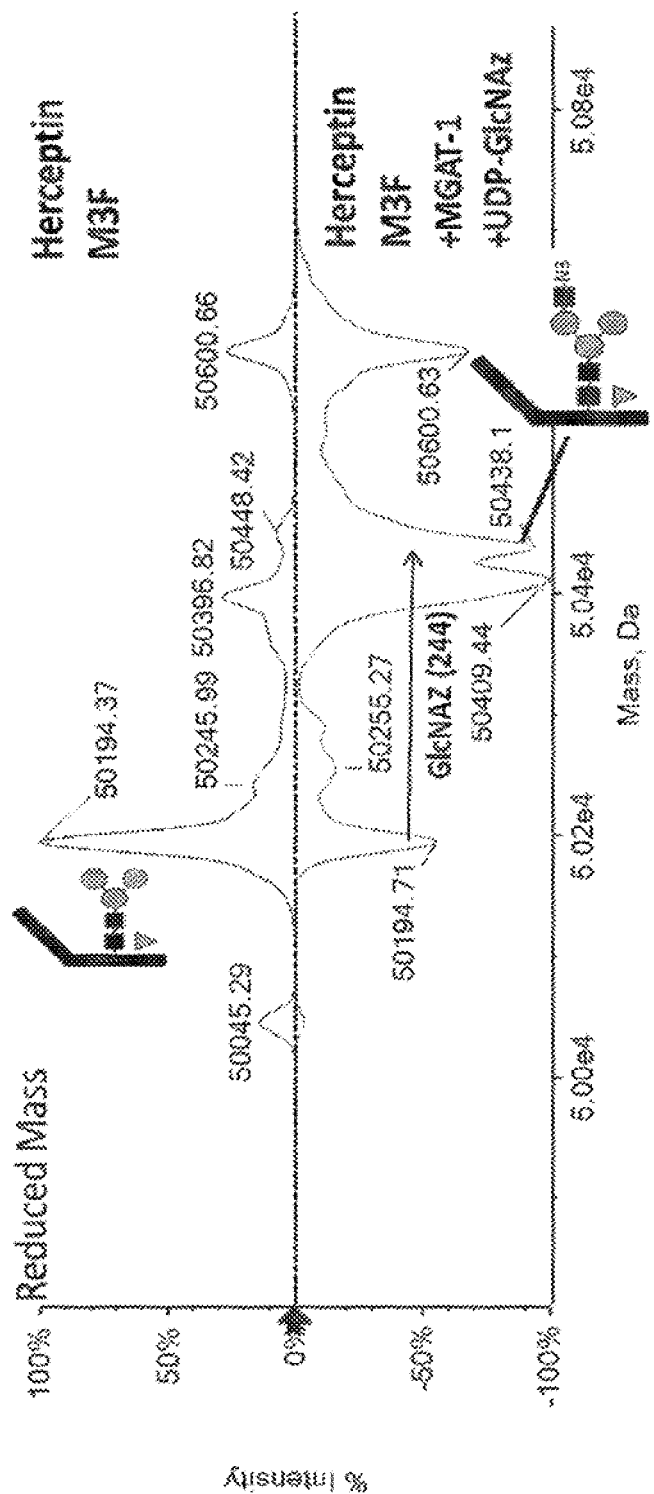
FIG. 6 shows the results of reduced mass chromatography analysis of Example 6. The result show that MGAT-1 conjugated UDP-GlcNAz to one arm of the terminal mannoses on each site of tri-mannosyl Herceptin.

Tri-mannosyl core Herceptin antibody (40 μg) from Example 2 and UDP-GlcNAz (1 mM) (R&D, ES104-100) in 80 μl 1× buffer (20 mM Tris, 10 mM MnCl₂, pH 6.5) were incubated in the presence of MGAT-1 (0.25 μg; R&D, 8334-GT) at 37° C. for 16 hours. The product was subjected to a Reduced Mass Chromatography analysis. As the results shown in the FIG. 6, compared to tri-mannosyl core Herceptin antibody having a heavy chain with a molecular weight of 50,195 Da, an antibody product, whose heavy chain contains one more GlcNAz (molecular weight of 244

Da) and has a molecular weight of 50,438 Da, was obtained.. This result suggests that UDP-GlcNAz is one of MGAT-1's substrates, and that through MGAT-1, GlcNAz can be linked to α-3 mannose in the arm of each heavy chain of tri-mannosyl core Herceptin antibody to form a tri-mannosyl Herceptin-2GlcNAz antibody.

Example 7. Conjugation of UDP-GlcNAz to Tri-Mannosyl Core Herceptin Antibody to Generate Tri-Mannosyl Herceptin-4GlcNAz by MGAT-1 and MGAT-2

Figure 7A:
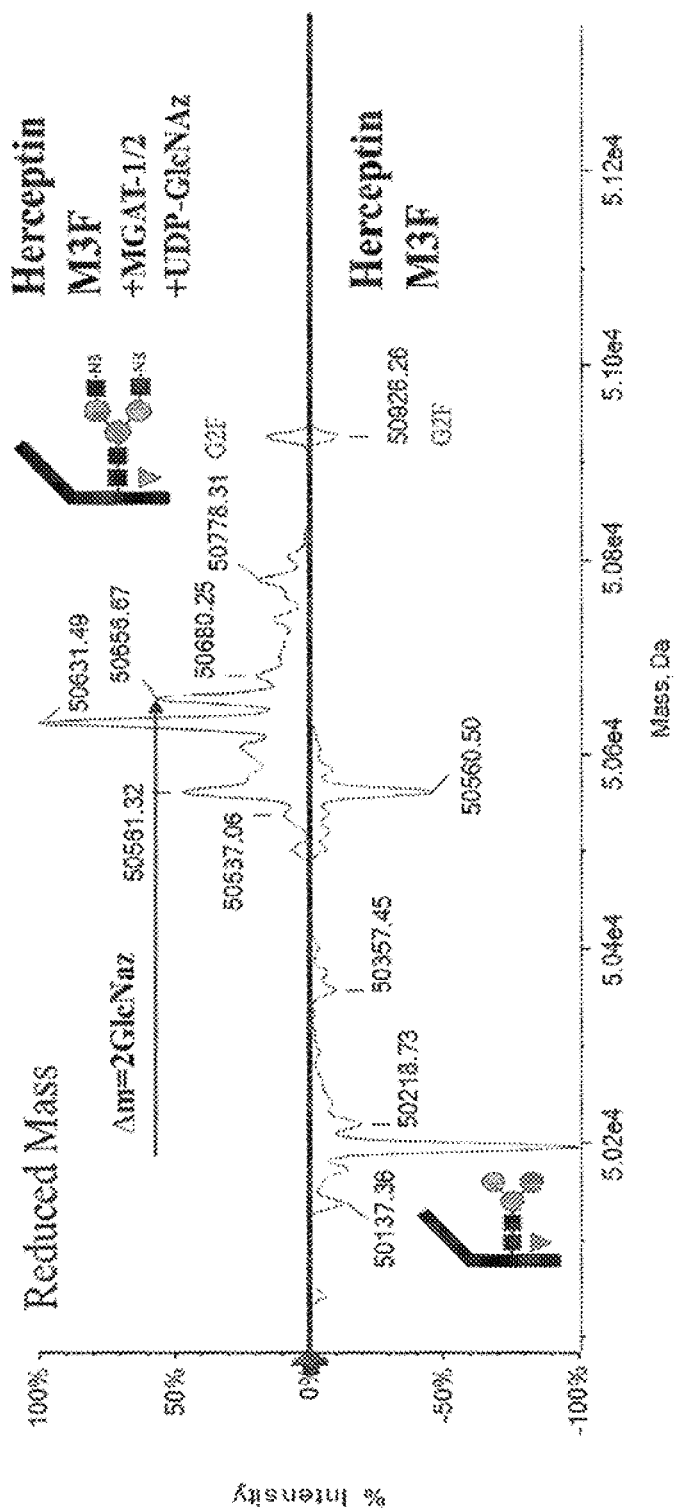
FIG. 7A shows the results of reduced mass chromatography analysis of Example 7.
Figure 7B:
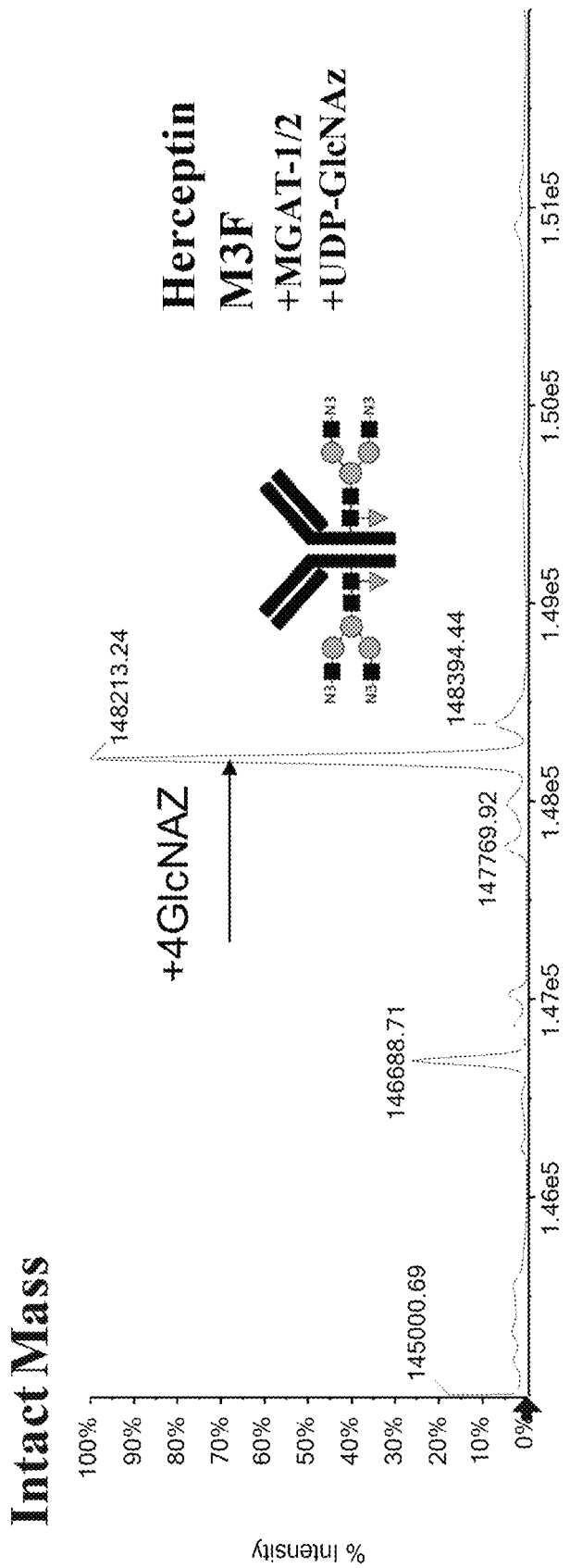
FIG. 7B shows the results of intact mass chromatography Analysis of Example 7. The results show that MGAT-1 and MGAT-2 conjugated UDP-GlcNAz to tri-mannosyl Herceptin to generate a G0F/G0 type Herceptin with 4 azide groups in the terminal N-acetyl-glucosamines.
Figure 7B:
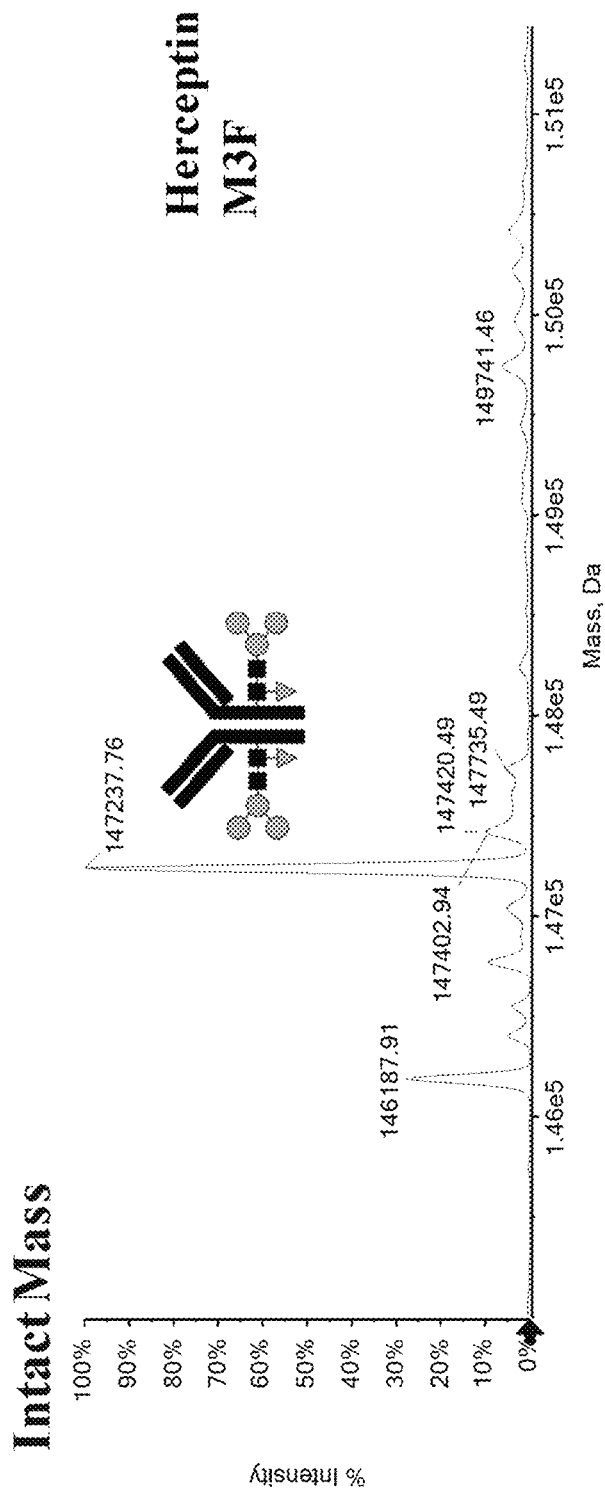

Tri-mannosyl core Herceptin antibody (2 mg) from Example 2 and UDP-GlcNAz (1 mM) in 800 μl 1× buffer SP (25 mM MES, 10 mM MnCl$_2$, pH 6.5) were incubated in the presence of rabbit MGAT-1 (25 μg) and rat MGAT-2 (10 μg) at 37° C. for 16 hours. After the incubation, the reaction product was subjected to a Reduced Mass Chromatography analysis and an Intact Mass Chromatography analysis, respectively. As the Reduced Mass Chromatography results shown in the FIG. 7A, compared to tri-mannosyl core Herceptin antibody having a heavy chain with a molecular weight of 50,194 Da, a tri-mannosyl Herceptin –4GlcNAz antibody product, wherein the heavy chains contain two GlcNAz molecules (molecular weight of 244 Da×2=488) and each heavy chain has a molecular weight of 50,680 Da, was obtained. This result suggests that through MGAT-1 and MGAT-2, GlcNAz is conjugated to α-3 mannose and α-6 mannose of each heavy chain of tri-mannosyl core Herceptin antibody. This result is further confirmed by the intact mass chromatography. As the results shown in the FIG. 7B, compared to the whole tri-mannosyl core Herceptin antibody with the molecular weight of 147,237 Da, a G0F tri-mannose Herceptin-4GlcNAz antibody product, which contains four GlcNAz molecules (molecular weight of 244 Da×4=976 Da) and has a molecular weight 148,213 Da, was obtained. Our results further support that UDP-GlcNAz is one of substrates of MGAT-1 and MGAT-2 and we can synthesize a intermediate tetra-Azido antibody in our one-step process hypothesis with success.

Figure 8:
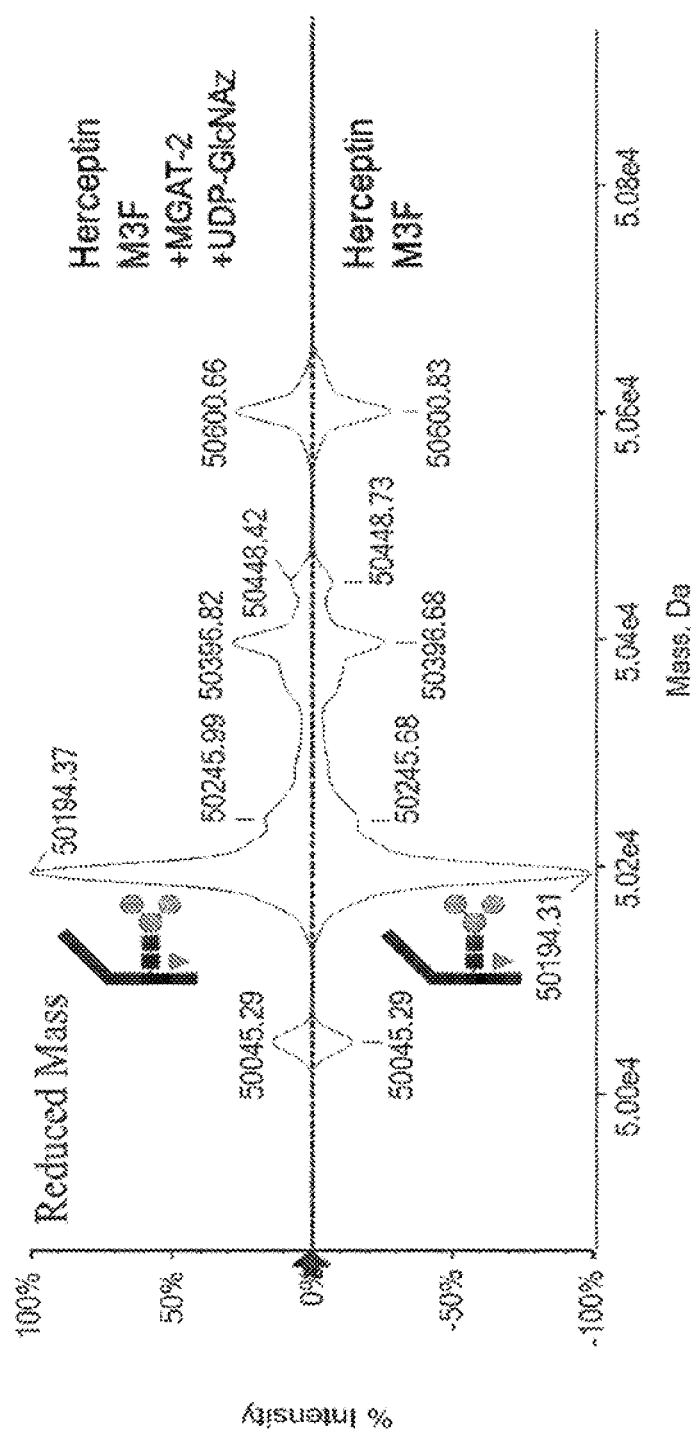
FIG. 8 shows the results of reduced mass chromatography analysis of Example 8. The results proves that that tri-mannosyl Herceptin is not the substrate of MGAT-2 for conjugating GlcNAz.

Example 8. Tri-Mannosyl Core Herceptin Antibody is not a Substrate of MGAT-2 to Conjugate GlcNAz Tri-mannosyl core Herceptin antibody (40 μg) from Example 2 and UDP-GlcNAz (1 mM) (R&D ES104-100) in 80 μl 1× buffer SP (25 mM MES, 10 mM MnCl$_2$, pH 6.5) were incubated in the presence of rat MGAT-2 (0.25 μg) at 37° C. for 16 hours. The product was subjected to a Reduced Mass Chromatography analysis. FIG. 8 shows that there is no significant change to the molecular weight of the tri-mannosyl core antibody in the Mass spectrum and suggests that as the result of Example 5 a tri-mannosyl antibody is not a substrate of MGAT-2.

Example 9. Conjugation of Tri-Mannosyl Herceptin-4GlcNAz Antibody with DBCO-(PEG)$_4$-DM1 to Produce a Herceptin ADC with DAR4

Figure 9A:
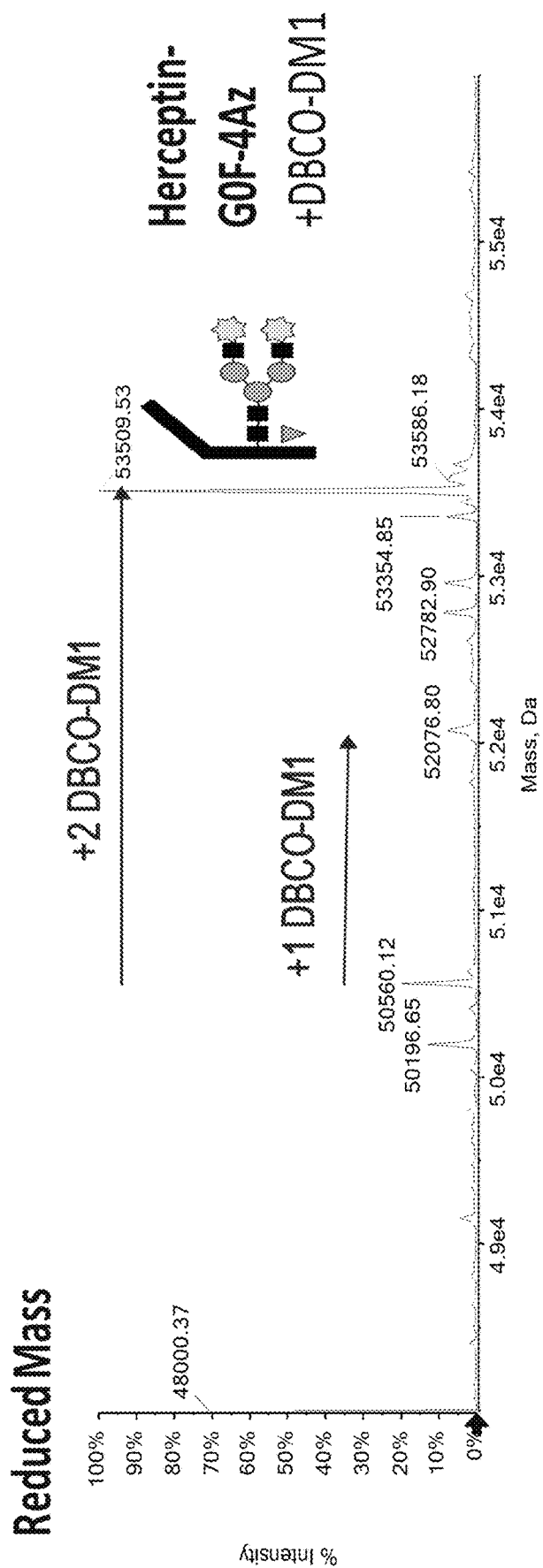
FIG. 9A shows the results of reduced mass chromatography analysis of Example 9.
Figure 9A:
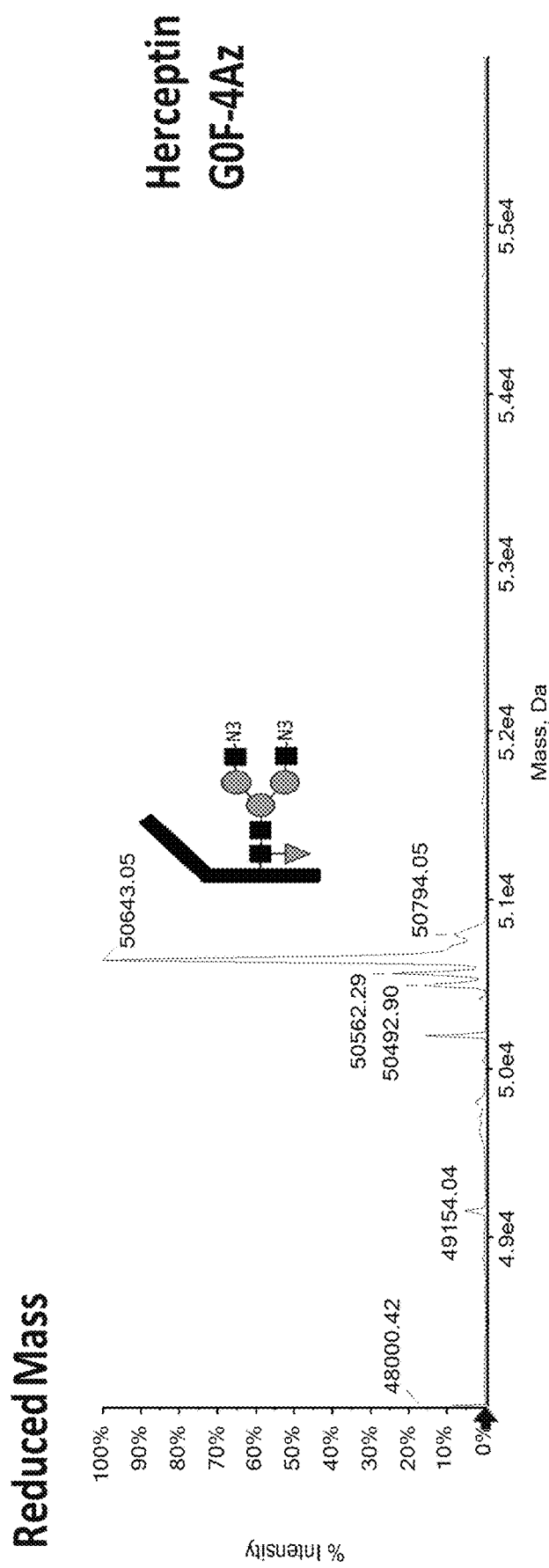
Figure 9B:
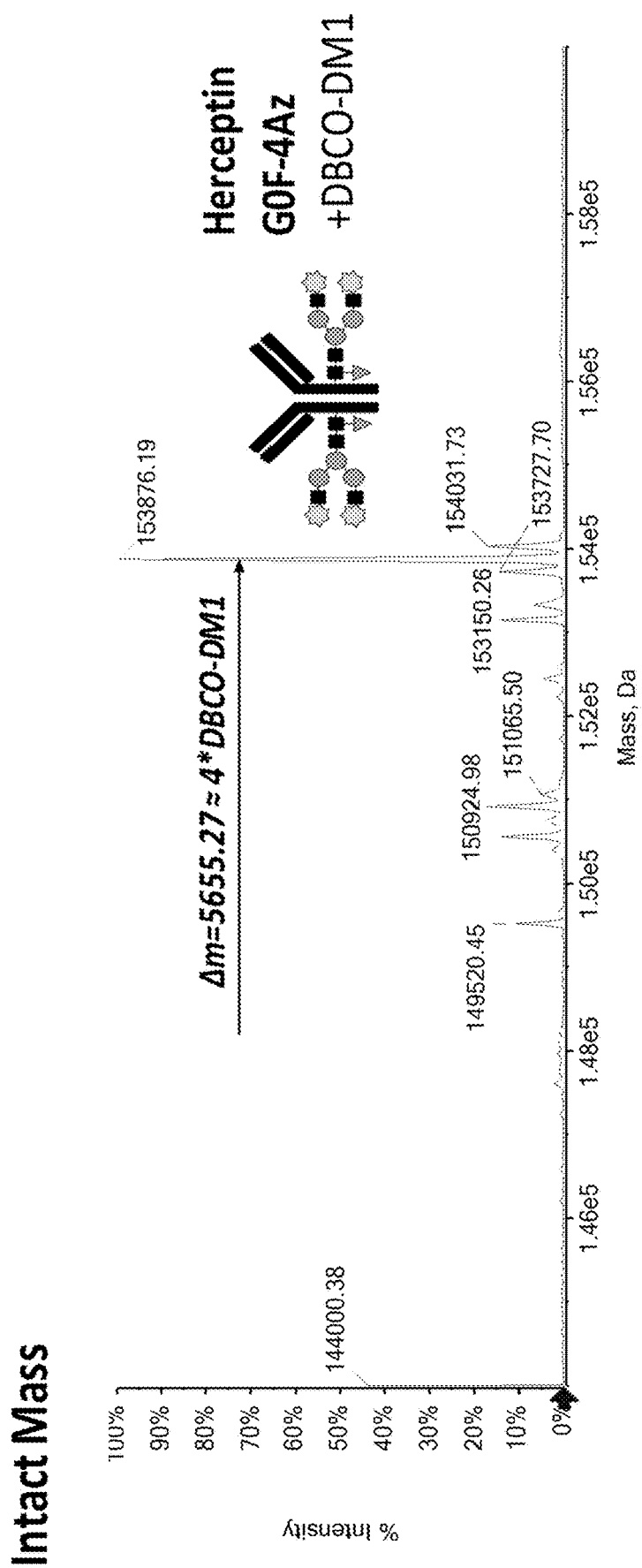
FIG. 9B shows the results of intact mass chromatography Analysis of Example 9. The results of the drawings show that DBCO-$(PEG)_4$-DM1 was conjugated to a tri-mannosyl Herceptin-4GlcNAz by click chemistry reaction to produce a Heceptin ADC with DAR4.
Figure 9B:
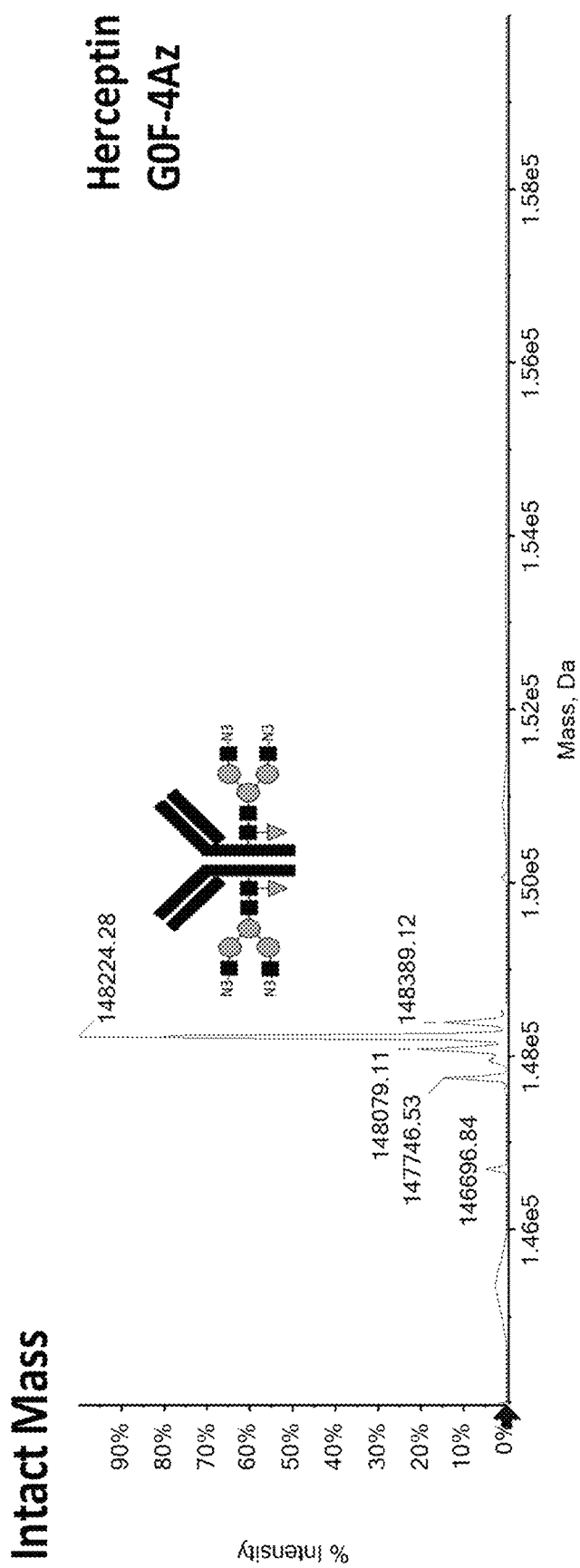

In Example 7, a tri-mannosyl antibody with each of 4 GlcNAz attached at 4 terminal mannoses was produced. To complete one-step process hypothesis of this invention, DBCO-(PEG)$_4$-DM1 was used to couple a toxic payload to the tri-mannosyl Herceptin-4GlcNAz to generate a ADC with DAR4. 5 μL of DBCO-(PEG)4-DM1 (10 mM in DMSO) was slowly added to 50 μL buffer (25 mM MES; pH 6.5) containing 5 mg/mL tri-mannosyl-4GlcNAz Herceptin antibody obtained from Example 7 to perform a click chemistry reaction at 25° C. for overnight. After reaction, the antibody product was purified through Amicon Ultra-15 centrifugal filter device to obtain tri-mannosyl Herceptin-4 (GlcNAc-triazole-DBCO-(PEG)4-DM1)ADC. The product was subjected to a Reduced Mass Chromatography analysis. The results in FIG. 9A reveal that by compared to its parent tri-mannosyl antibody with 4 GlcNAz, the heavy chain of the reaction product, tri-mannosyl Herceptin-4(GlcNAc-triazole-DBCO-(PEG)$_4$-DM1), has a molecular weight of 53,509 Da which means that two DBCO-(PEG)$_4$-DM1 molecules (molecular weight of 1,413 Da×2=2,826) have been conjugated to each heavy chain of the antibody. This result is further confirmed by the intact mass chromatography analysis. The results in the FIG. 9B reveal that compared to the tri-mannosyl Herceptin-4GlcNAz antibody with the molecular weight about 148,224 Da, a tri-mannosyl Herceptin-4(GlcNAc-triazole-DBCO-(PEG)$_4$-DM1) ADC product, which contains four DBCO-(PEG)4-DM1 molecules (molecular weight of 1,413 Da×4=5,652 Da) and has a molecular weight of 153,876 Da, was obtained. The results from Examples 7 and 9 indicate that an ADC-4DM1 product is produced from a tri-mannosyl antibody by directly combining MGAT-1, MGAT-2 and GlcNAz reactions and a DBCO-(PEG)$_4$-DM1 click chemistry reaction. Therefore, we successfully rationalize our hypothesis of one-step process for ADC generation in this invention.

Example 10. Conjugation of a First Payload to Terminal GlcNAz in Each Arm of the Heavy Chains of Tri-Mannosyl Herceptin-2GlcNAz by DBCO-(PEG)$_4$-DM1

Figure 10:
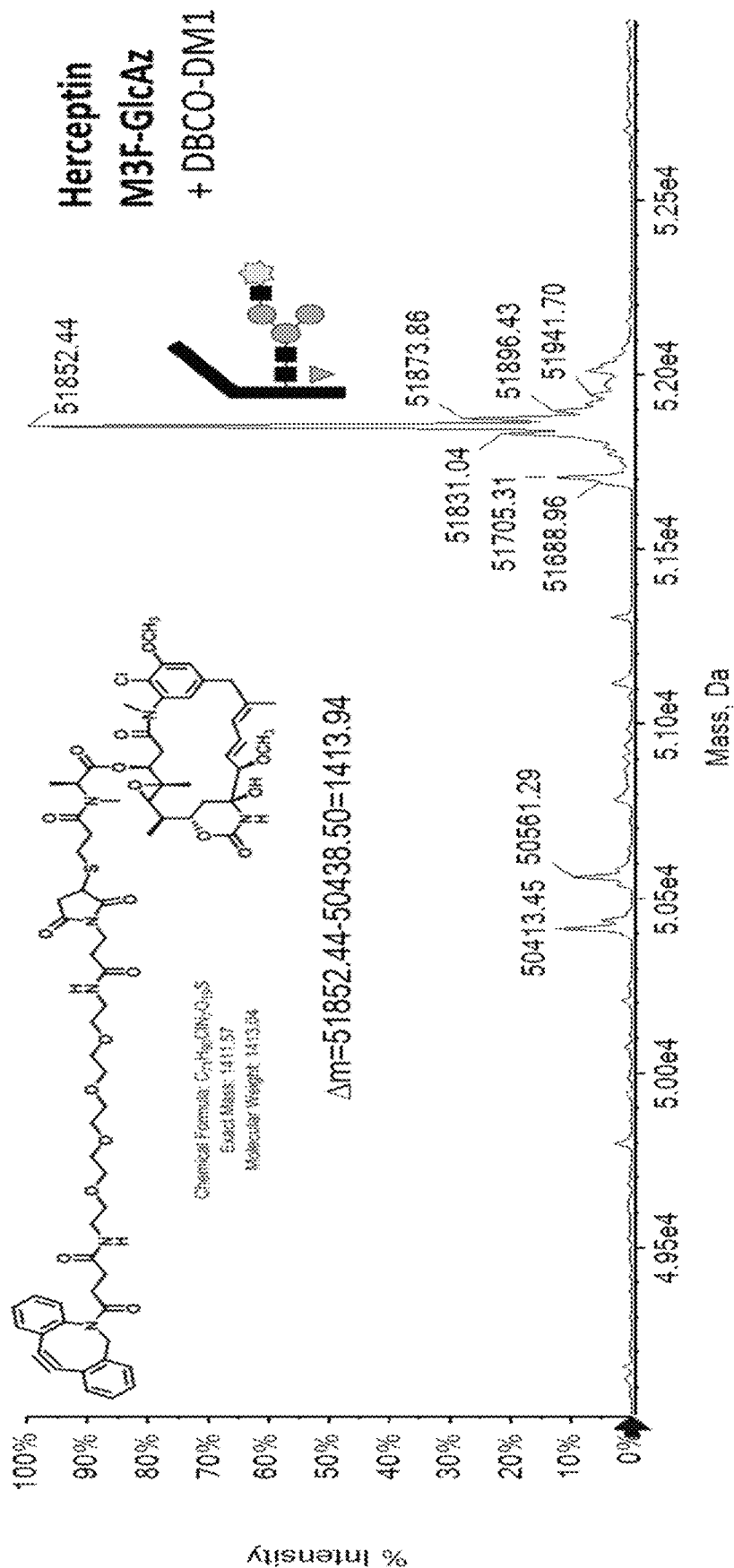
FIG. 10 shows the results of reduced mass chromatography analysis of Example 10. The results of the drawing show that the first payload conjugated to each arm of the heavy chains of tri-mannosyl-2GlcNAz Herceptin antibody by MGAT-1 and DBCO-$(PEG)_4$-DM1.

Examples 4 to 9 support the feasibility of one-step process for ADC generation in this invention to generate a site-specific ADC with homogenous DAR of 4. With these successful results, a study was performed to prove the sequential process shown in FIG. 1. To synthesize the first intermediate product, DBCO-(PEG)4-DM1 was used to couple the payload to attach each terminal GlcNAz of heavy chain of reactant antibody. 14 μL of DBCO-(PEG)$_4$-DM1 (10 mM in DMSO) was slowly added to 350 μL buffer (25 mM MES; pH 6.5) containing 2 mg/mL tri-mannosyl Herceptin-2GlcNAz antibody obtained from Example 6. The reaction mixture was stirred under argon at 25° C. overnight to perform a click chemistry reaction. After the reaction, the antibody product was filtrated through an Amicon Ultra-15 centrifugal filter device to obtain a tri-mannosyl Herceptin-2(GlcNAc-triazole-DBCO-(PEG)$_4$-DM1) intermediate. The product was subjected to a reduced mass chromatography analysis. As the results shown in the FIG. 10, compared to tri-mannosyl Herceptin-2GlcNAz antibody, one arm of the heavy chains of the tri-mannosyl Herceptin-2(GlcNAc-triazole-DBCO-(PEG)$_4$-DM1) intermediate with a molecular weight of 51,852 Da contains one additional DBCO-(PEG)$_4$-DM1 molecule with a molecular weight of 1414 Da.

Example 11. Conjugation of a Second GlcNAz to Terminal α-6 Mannose in Each Arm of the Heavy Chain of Tri-Mannosyl Herceptin-2(GlcNAc-Triazole-DBCO-(PEG)4-DM1) ADC by MGAT-2

Figure 11:
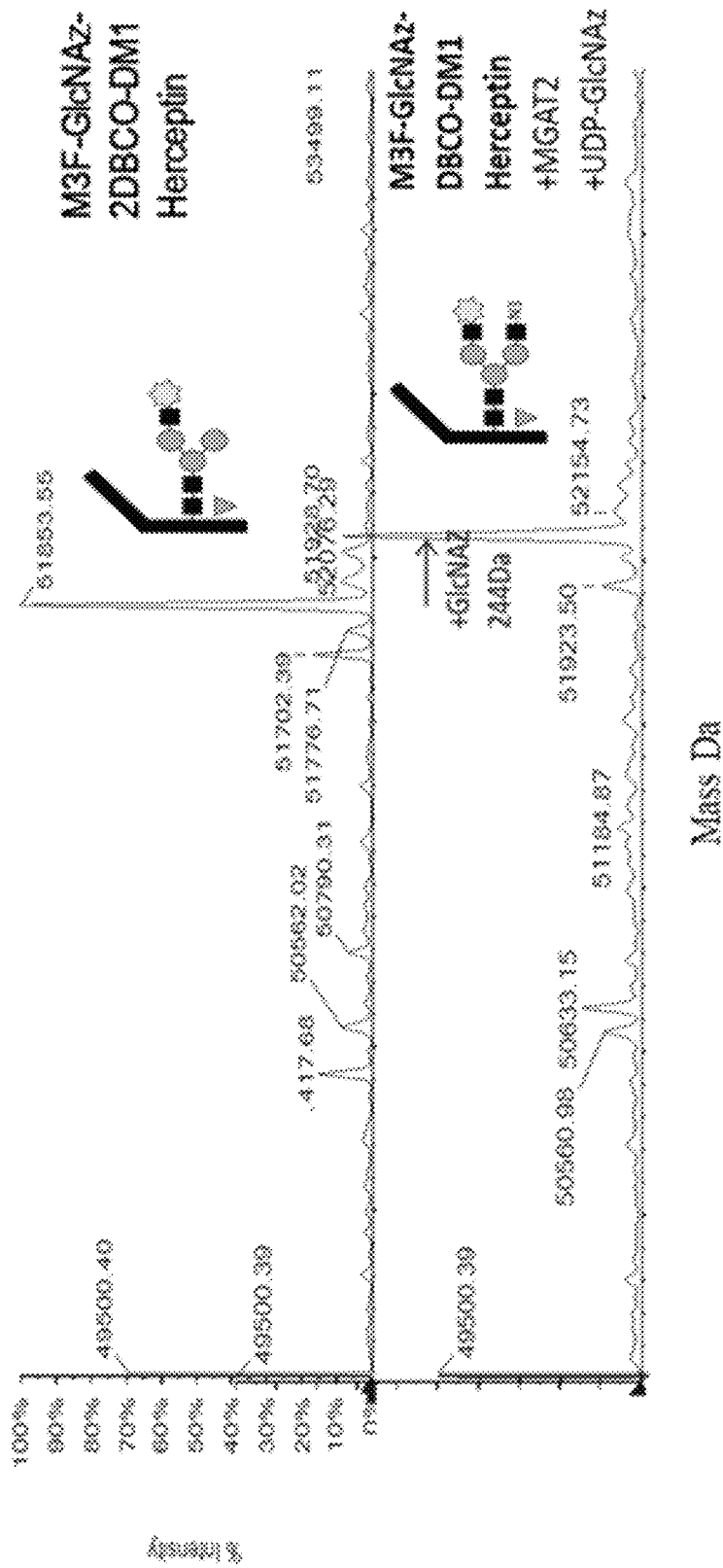
FIG. 11 shows the results of reduced mass chromatography analysis of Example 11. The results of the drawing show that the second GlcNAz conjugated to α-6 mannose to each arm of the heavy chain of tri-mannosyl Herceptin-2 (GlcNAc-triazole-DBCO-(PEG)4-DM1) ADC by MGAT-2. This suggests that MGAT-2 is a very substrate flexible enzyme and converts UDP-GlcNAz to a large functional group antibody such as tri-mannosyl Herceptin-2(GlcNAc-triazole-DBCO-(PEG)4-DM1) to generate an intermediate for a dual payload ADC product.

The tri-mannosyl Herceptin-2GlcNAz-2(GlcNAc-triazole-DBCO-(PEG)4-DM1) obtained from Example 10 and UDP-GlcNAz (1 mM) (R&D ES104-100) in 500 μl 1× buffer (25 mM MES, 10 mM MnCl$_2$, pH 6.5) were incubated in the presence of rat MGAT-2 (15 µg) at 37° C. for 16 hours. After reaction, the antibody product was filtrated through Amicon Ultra-15 centrifugal filter device to obtain tri-mannosyl Herceptin-2GlcNAz-2(GlcNAc-triazole-DBCO-(PEG)$_4$-DM1). The product was subjected to a Reduced Mass Chromatography analysis. As the results shown in the FIG. 11, compared to the parent tri-mannosyl Herceptin-2 (GlcNAc-triazole-DBCO-(PEG)$_4$-DM1), each of the heavy chains of the tri-mannosyl Herceptin-2GlcNAz -2(GlcNAc-triazole-DBCO-(PEG)$_4$-DM1) contains one additional GlcNAz molecule (MW=244) with a molecular weight of 52,097 Da. This result indicates that MGAT-2 is a very substrate flexible enzyme and converts UDP-GlcNAz to a large functional group antibody such as tri-mannosyl Herceptin-2(GlcNAc-triazole-DBCO-(PEG)$_4$-DM1) to generate a intermediate for a dual payload ADC product.

Example 12. Construction of a DAR4 ADC Herceptin Product with One MMAE and One DM1 on Each Arm of the Antibody In Example 11, a tri-mannosyl Herceptin-2GlcNAz-2 (GlcNAc-triazole-DBCO-(PEG)$_4$-DM1) intermediate was produced. To complete the sequential process of this invention shown in FIG. 1, DBCO-(PEG)$_{12}$-MMAE was used to couple a toxic payload to the tri-mannosyl Herceptin-2GlcNAz 2(GlcNAc-triazole-DBCO-(PEG)$_4$-DM1) and generate a ADC with DAR4 and dual species of payloads.

Figure 12:
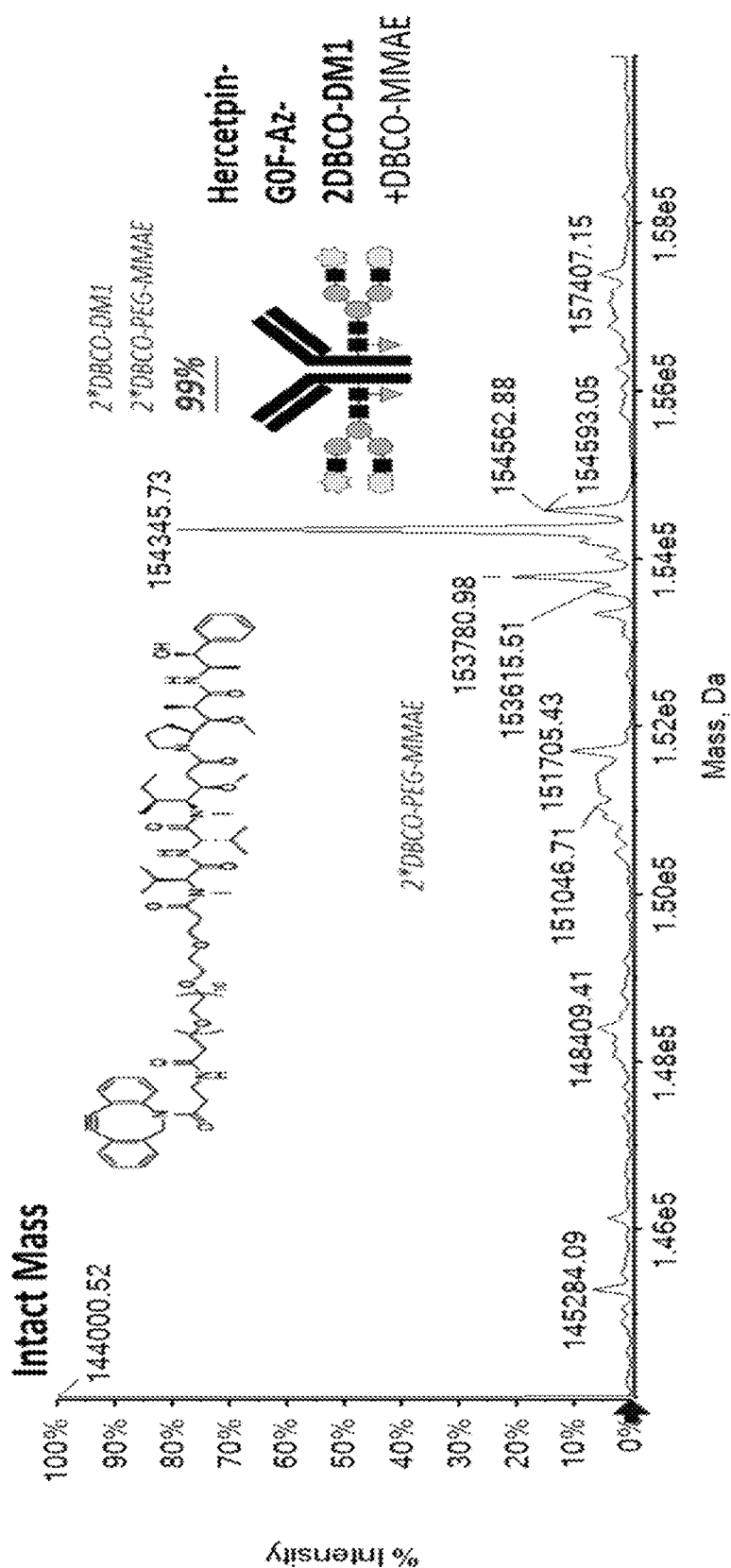
FIG. 12 shows the results of intact mass chromatography Analysis of Example 12. The results of the drawing show that a DAR4 ADC Herceptin product with one MMAE and one DM1 on each arm of antibody was generated by adding DBCO-$(PEG)_{12}$-MMAE to the intermediate tri-mannosyl Herceptin-2GlcNAz-2(GlcNAc-triazole-DBCO-(PEG)4-DM1) produced from the product of Example 11.

3.8 µL of DBCO-(PEG)$_{12}$-MMAE (10 mM in DMSO) was slowly added to 76 µL 1× buffer (25 mM MES, pH 6.5) containing 2.5 mg/mL tri-mannosyl Herceptin-2GlcNAz-2 (GlcNAc-triazole-DBCO-(PEG)4-DM1) ADC obtained from Example 11. The reaction mixture was stirred under argon at 25° C. overnight to preform a click chemistry reaction. After the reaction, the antibody product was filtrated through Amicon Ultra-15 centrifugal filter device to obtain tri-mannosyl Herceptin-2(GlcNAc-triazole-DBCO-(PEG)$_4$-DM1)-2(GlcNAc-triazole-DBCO-(PEG)$_{12}$-MMAE) ADC. After the purification, the product was then subjected to an intact mass chromatography analysis. As the results shown in the FIG. 12, compared to the parent tri-mannosyl Herceptin-2GlcNAz-2(GlcNAc-triazole-DBCO-(PEG)$_4$-DM1) with a molecular weight of 151,050 kD, the obtained tri-mannosyl Herceptin-2(GlcNAc-triazole-DBCO-(PEG)$_4$-DM1)-2(GlcNAc-triazole-DBCO-(PEG)$_{12}$-MMAE) ADC contains two additional DBCO-(PEG)$_{12}$-MMAE molecules (MW=1648×2=3,296) and has a molecular weight of 154,345 Da. This result suggests that the method of invention can precisely control the conjugation of two different payloads (e.g., DBCO-PEG$_4$-DM1 and DBCO-(PEG)$_{12}$-MMAE) to tri-mannosyl Herceptin.

Figure 13:
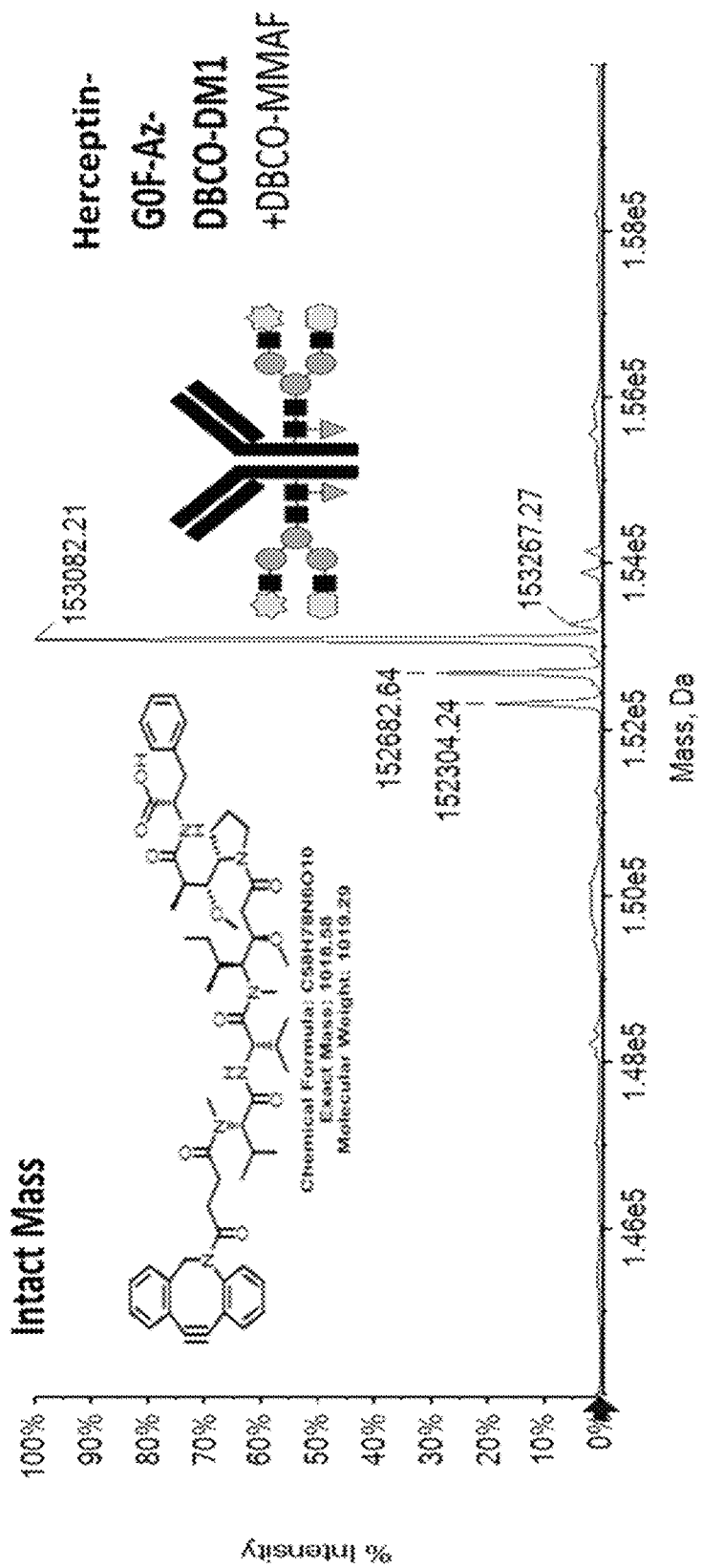
FIG. 13 shows the results of intact mass chromatography Analysis of Example 13. The results show that a DAR4 ADC Herceptin product with one MMAF and one DM1 on each arm of antibody was generated by adding DBCO-MMAF to an intermediate tri-mannosyl Herceptin-2GlcNAz-2 (GlcNAc-triazole-DBCO-(PEG)4-DM1) produced from the product of Example 11.

Example 13. Construction of a DAR4 ADC Herceptin Product with One MMAF and One DM1 on Each Arm of the Antibody 3.8 µL of DBCO-MMAF (10 mM in DMSO) was slowly added to 76 µL 1× buffer (25 mM MES, pH 6.5) containing 2.5 mg/mL tri-mannosyl Herceptin-2GlcNAz-2(GlcNAc-triazole-DBCO-(PEG)4-DM1) ADC obtained from Example 11. The reaction mixture was stirred under argon at 25 overnight to perform a click chemistry reaction. After the reaction, the antibody product was filtrated through Amicon Ultra-15 centrifugal filter device to obtain tri-mannosyl Herceptin-2(GlcNAc-triazole-DBCO-(PEG)$_4$-DM1)-2 (GlcNAc-triazole-DBCO-MMAF) ADC. The product was subjected to an intact mass chromatography analysis. As the results shown in the FIG. 13, compared to the parent tri-mannosyl Herceptin-2GlcNAz-2(GlcNAc-triazole-DBCO-(PEG)$_4$-DM1) ADC (MW=151,050), the obtained tri-mannosyl Herceptin-2(GlcNAc-triazole-DBCO-(PEG)$_4$-DM1)-2(GlcNAc-triazole-DBCO-MMAF) ADC contains two additional DBCO-MMAF molecules with a molecule are weight of 2,038 D and has a molecular weight of 153,082 Da. This result suggests that the method of invention can precisely control the conjugation of variable species of payloads (e.g., DBCO-(PEG)$_4$-DM1, DBCO-(PEG)$_{12}$-MMAE and DBCO-MMAF) to tri-mannosyl Herceptin.

In summary, by combining MGAT-1, MGAT-2, and GlcNAz enzymatic reactions and DBCO-payload chemistry reactions, we rationalize our hypothesis of the invention. We are able to generate a homogenous site-specific ADC product with DAR4 or DAR2 by our one-step process. On the other hand, the invention is also applied to synthesize a homogenous site-specific ADC product with dual species of payloads by the sequential process.

Example 14. Binding Affinity Analysis of Tri-Mannosyl Herceptin-4(GlcNAc-Thiazole-DBCO-(PEG)$_4$-DM1)

Figure 14:
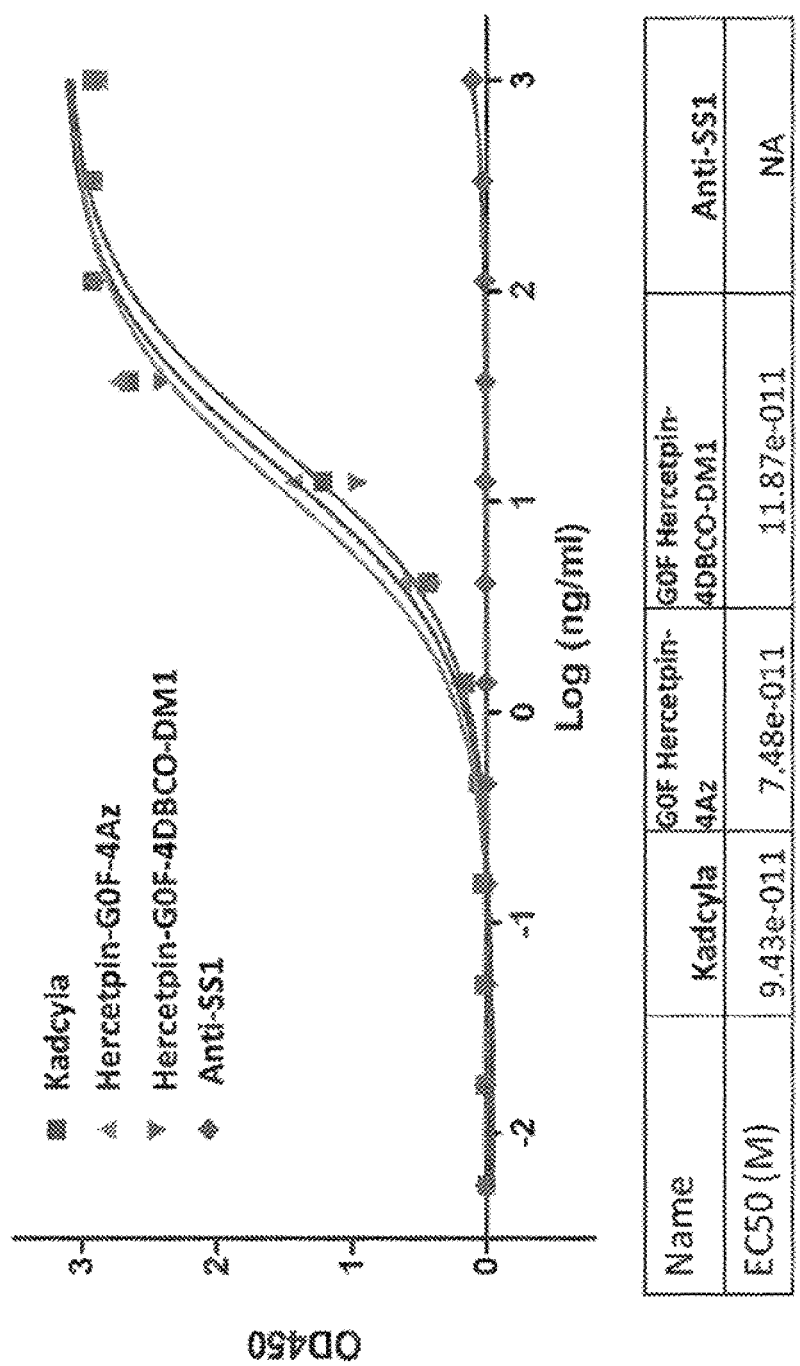
FIG. 14 shows the binding ELISA of Kadcyla and tri-mannosyl Herceptin-4(GlcNAc-triazole-DBCO-(PEG)4-DM1) as described in Example 14. The results indicates that there was no significant Kd difference between Kadcyla and the tri-mannosyl Herceptin-4(GlcNAc-triazole-DBCO-(PEG)4-DM1) product.

A tri-mannosyl Herceptin-4(GlcNAc-triazole-DBCO-(PEG)$_4$-DM1) ADC was constructed by the processes described above. Kadcyla against Her2/Neu molecule was purchased from (Roche Inc). ERBB2-ECD (ebioscience BMS362) (100 ng/well) was added to each well of a NUNC Maxisorp plate and the plate was set aside at 4° C. overnight. The plate was washed with 1×PBS-T (0.1%) to remove the uncoated reagent. 3% skim milk was added to the wells of the plate, and the plate was set aside at room temperature for 2 hours. The plate was washed with 1×PBS-T (0.1%) for 3 times, was allowed to dry and then was stored at −20° C. for further use. A series of dilutions from 1×10$^6$ g/mL to 1×10$^{-12}$ g/mL of individual antibodies were added to the plate, and the plate was incubated at 370 C for 1 hour. A goat anti-human IgG conjugated with horseradish peroxidase (HRP) was added for 1 hour incubation, and then 3,3',5,5'-Tetramethylbenzidine (TMB) was added. The OD405 was read to calculate the activity. Every study was repeated three times, and the data were presented as mean±SD. OD readings and concentrations of antibodies were used to make a multiple scatter plot using Prism™ software. The results shown in FIG. 14 reveal that the curve of tri-mannosyl Herceptin-4(GlcNAc-triazole-DBCO-(PEG)4-DM1) ADC was almost the same as those of the positive controls Kadcyla and tri-mannosyl Herceptin-4GlcNAz. The negative control anti-mesothelien shows no binding affinity to Her2/Neu molecule. This result suggests that the binding affinity of tri-mannosyl Herceptin-4(GlcNAc-triazole-DBCO-(PEG)4-DM1) ADC to the Her2/Neu molecule is not affected by the modifications made.

Example 15. Cytotoxic Effect of Tri-Mannosyl Herceptin-4(GlcNAc-Triazole-DBCO-(PEG)4-DM1) ADC Her2/Neu high-expression cell line SK-BR-3, Her2/Neu medium-expression cell line HCC-1954 and Her2/Neu low-expression cell line MDA-MB-231 were diluted to 10$^6$ cells/nil. After adding 100 µL of the diluted cell culture to the wells of a 96-well plate, the cells were incubated at 37° C. for 24 hours. 80 nl complete medium was added to each well, and 200 tri-mannosyl Herceptin-4(GlcNAc-triazole- DBCO-(PEG)4-DM1) ADC in different doses was then added to different wells. After the plate being incubated at 37° C. for 48 hours, 100 nl the CellTiter-Glo® Reagent was added to each wells. After further incubation for 10 minutes at room temperature, luminescence (light) of the wells was measured by a luminometer. The IC50 values of tri-mannosyl Herceptin-4(GlcNAc-triazole-DBCO-(PEG)$_4$-DM1) ADC to Her2/Neu high-expression cell line SK-BR-3, and Her2/Neu medium-expression cell line HCC-1954 were 4.7 nM and 14 nM, respectively. The IC50 values also show that all the antibodies tested had no anti-proliferation effects on the Her2/Neu low-expression cell line MDA-MB-231. This result suggests that as Kadcyla, the tri-mannosyl Herceptin-4(GlcNAc-triazole-DBCO-(PEG)$_4$-DM1) ADC does not only have cytoxicity to the Her2/Neu high expressing cells, but also the Her2/Neu medium expressing medium-expression cells and the modification of antibody by tri-mannosyl ADC platform does not affect the its biological activity.

Figure 15A:
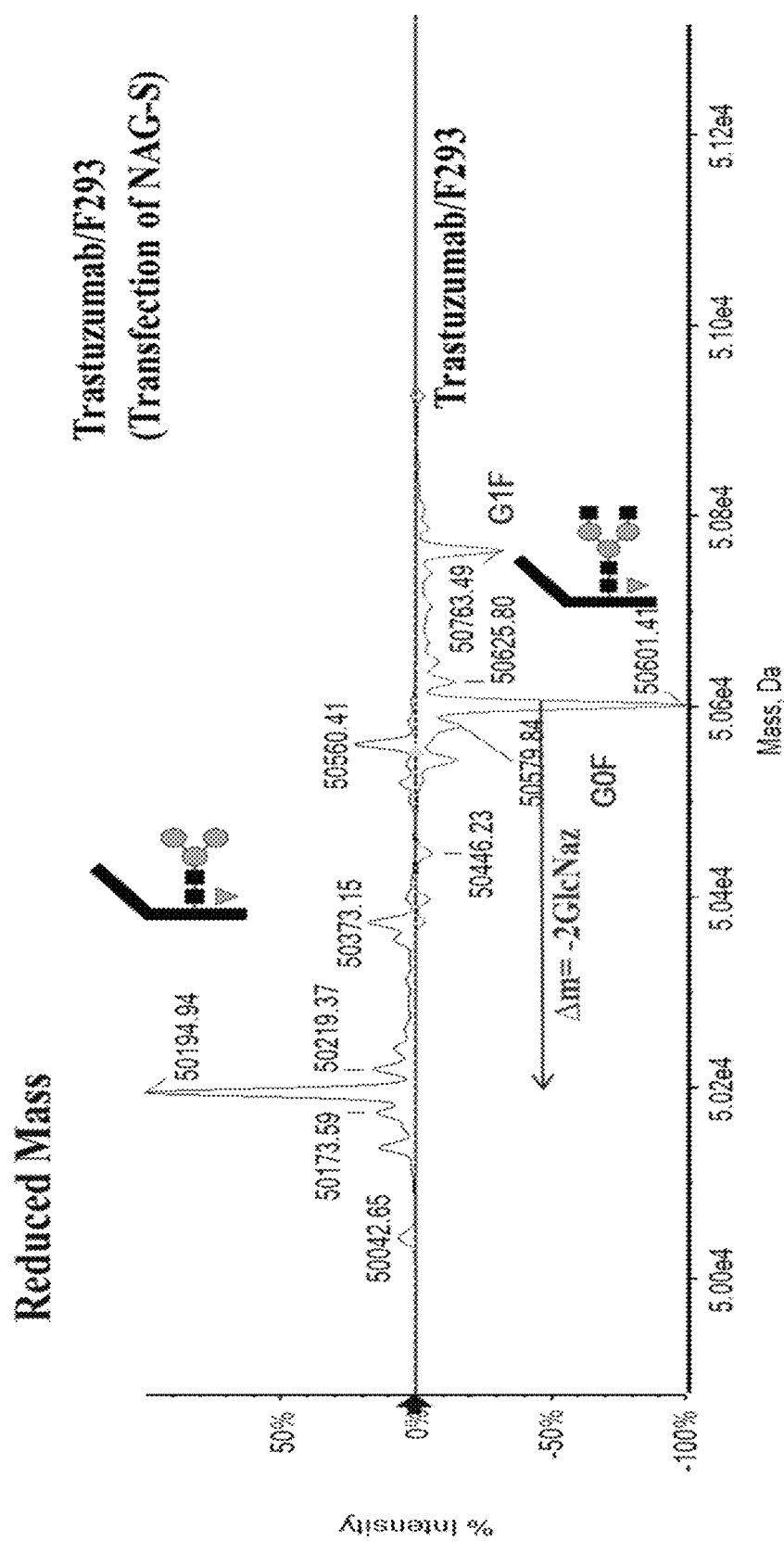
FIG. 15A and FIG. 15B show the results of reduced mass chromatography analysis of tri-mannosyl core trastuzumab antibodies of Example 16. The results show tri-mannosyl trastuzumab and trimannosyl anti TMCC3 were generated by a mammalian cell line.
Figure 15B:
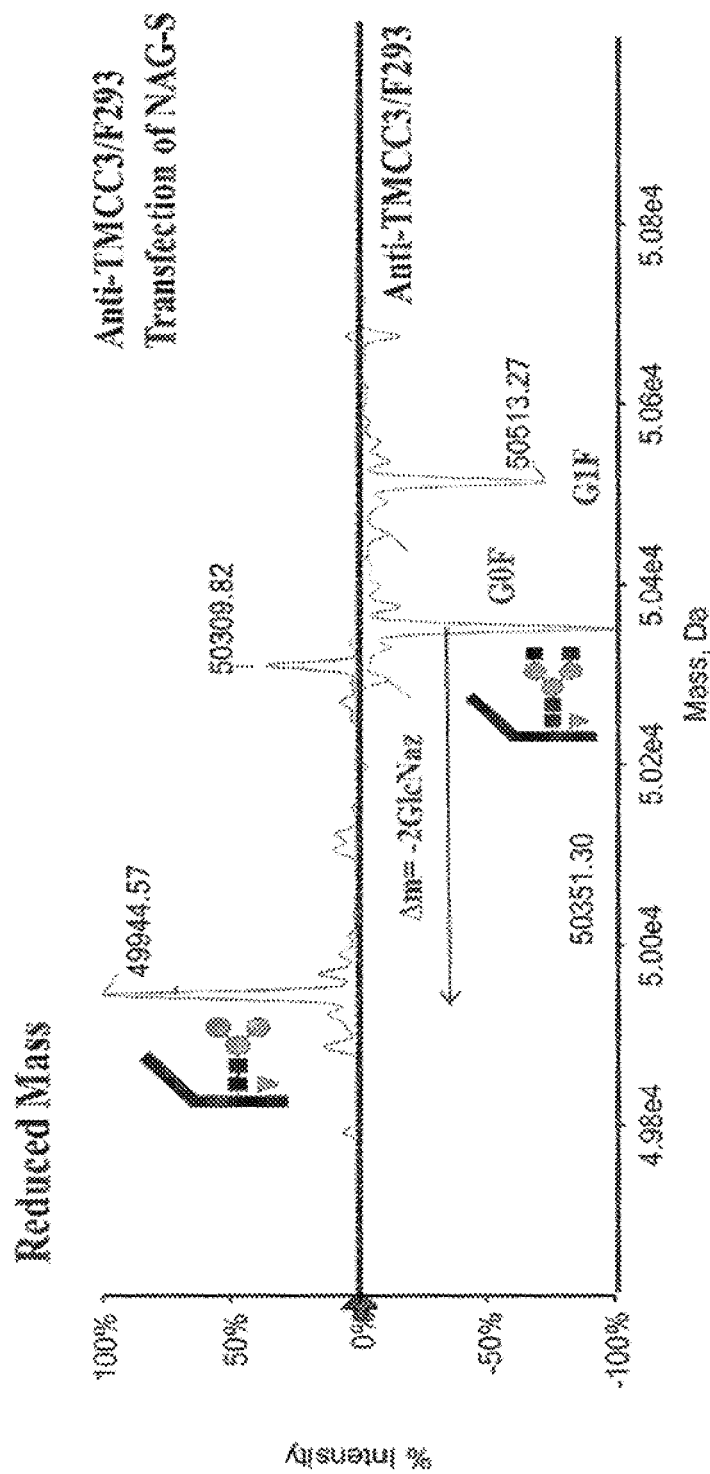

Example 16. Production of Tri-Mannosyl Core Trastuzumab Antibody and Tri-Mannosyl Core Anti-TMC33 Antibody by F293 Cells A plasmid pTCAE8.3-exo-Gal containing a cDNA encoding β-N-acetylglucosaminidase S was constructed and co-transfected into two F293 cell lines to express tri-mannosyl trastuzumab (an anti-Her2 antibody) and tri-mannosyl anti-TMCC3 (transmembrane and coiled-coil domain family 3) antibody, respectively. After incubation, the supernatants of the two cell cultures were collected and the antibodies contained therein were purified by using rProtein A Sepharose™ Fast Flow (GE Healthcare, 17-1279-02), respectively. After purification, the purified antibody samples were subjected to Reduced Mass Chromatography Analysis. The results shown in FIG. 15A reveal that when compared to the antibody isolated from the F293 cells transfected only trastuzumab gene, the heavy chain of the trastuzumab antibody obtained from the same cell also transfected with β-N-acetylglucosaminidase S and trastuzumab genes shows a peak with a molecular weight of 50,195 Da, which indicates that the resulting trastuzumab antibody was a trimannosyl core antibody. Similar results are seen in the same cell transfected with the anti-TMCC3 antibody gene (FIG. 15B). The results suggest that tri-mannosyl antibody is feasible to mass-produced from a commercial cell line and applied to industry CMC amplification.

Example 17. Conjugation of UDP-GlcNAz to Cell-Expressed Tri-Mannosyl Core Trastuzumab Antibody to Generate Tri-mannosyl Herceptin-4 (GlcNAc-Triazole-DBCO-(PEG)$_4$-DM1) ADC by MGAT-1 and MGAT-2

Figure 16A:
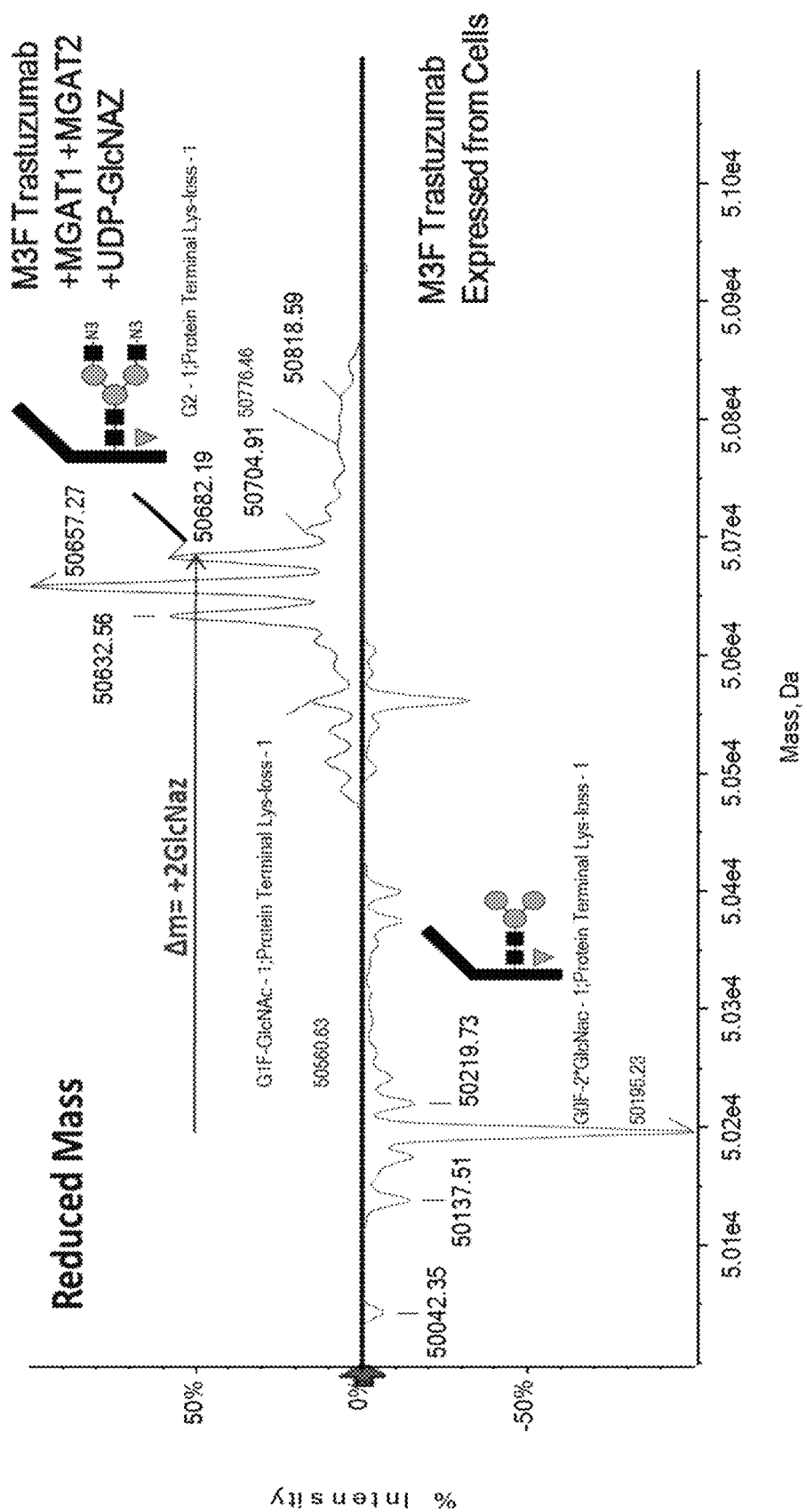
FIGS. 16A, 16B and 16C show the results of reduced mass chromatography analysises and intact mass chromatography analysis of Example 17. The results of the drawings show that tri-mannosyl Trastuzumab-4(GlcNAc-triazole-DBCO-(PEG)4-DM1) was generated from a mammalian cell producing tri-mannosyl trastuzumab.

According to the processes described in Example 7, 2 mg of tri-mannosyl core trastuzumab antibody (produced by mammalian cells) obtained from Example 16 and UDP-GlcNAz (1 mM) in 800 μl 1× buffer SP (25 mM MES, 10 mM MnCl$_2$, pH 6.5) were incubated in the presence of rabbit MGAT-1 (25 μg) and rat MGAT-2 (10 μg) at 37° C. for 16 hours. After the incubation, the reaction product was subjected to a reduced mass chromatography analysis and an intact mass chromatography analysis. As the reduced mass chromatography results shown in the FIG. 16A, compared to tri-mannosyl core trastuzumab antibody having a heavy chain with a molecular weight of 50,194 Da, a tri-mannosyl trastuzumab-4GlcNAz antibody product, which the heavy chains contain two more GlcNAz molecules with molecular weight of about 244 Da×2=488 and each heavy chain has a molecular weight of about 50,680 Da, was obtained. This result suggests that through MGAT-1 and MGAT-2, GlcNAz can be conjugated to α-3 mannose and α-6 Mannose of each heavy chain of tri-mannosyl core trastuzumab antibody produced by mammalian cells.

Figure 16B:
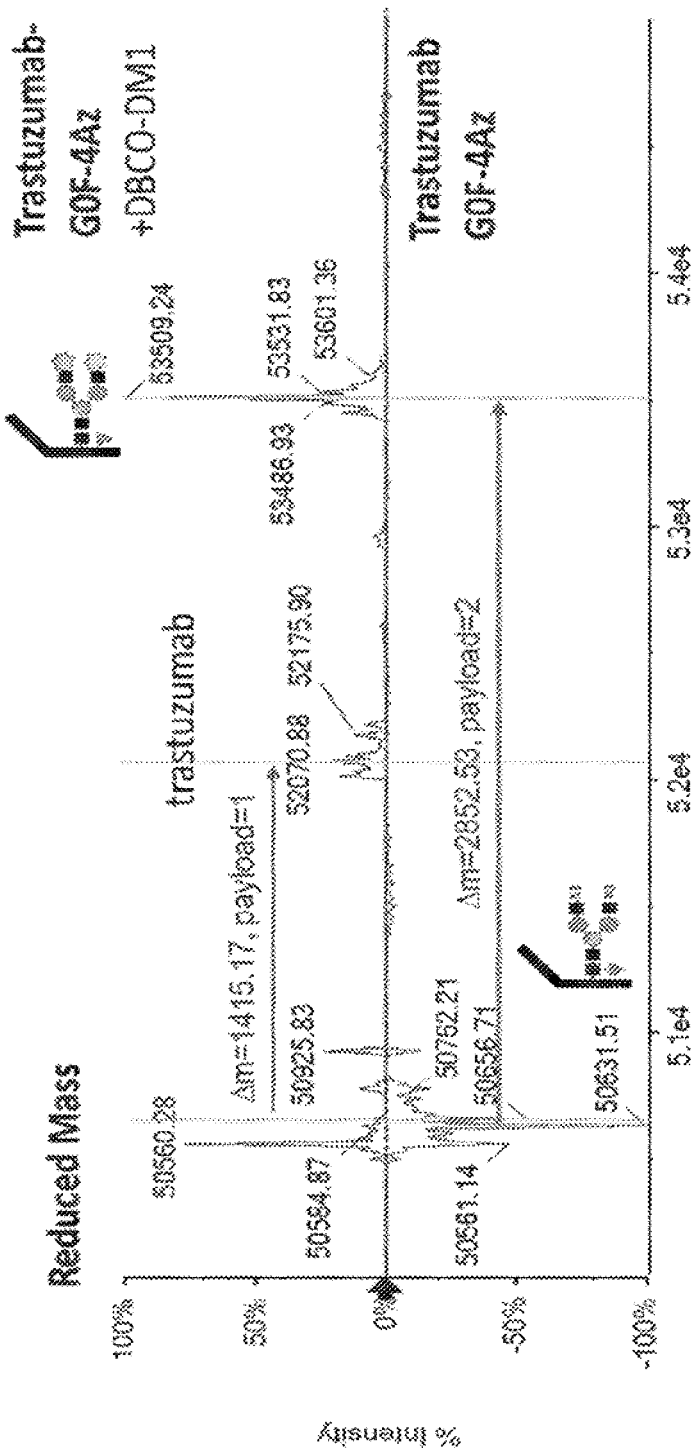
Figure 16C:
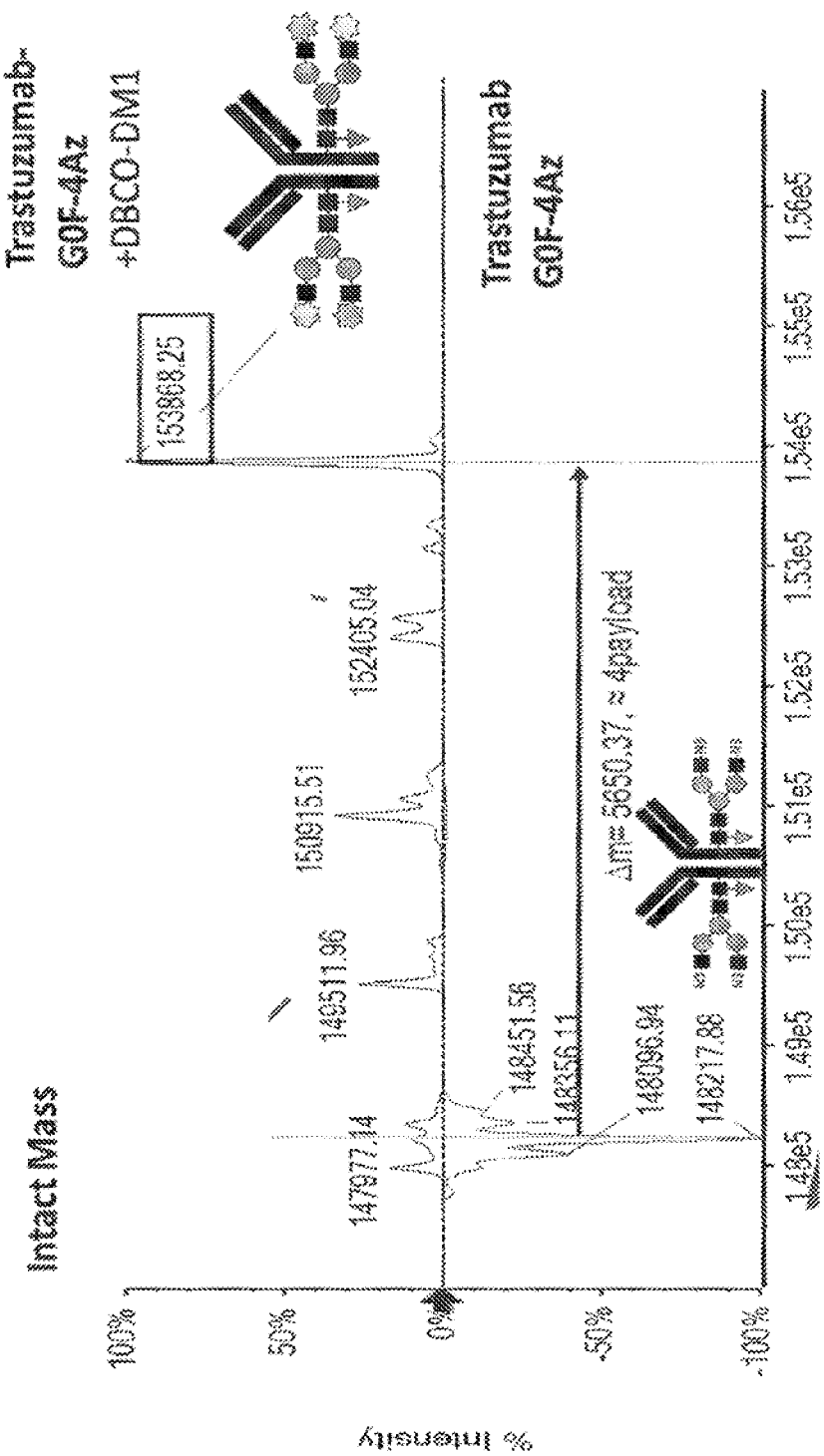
Figure 17:
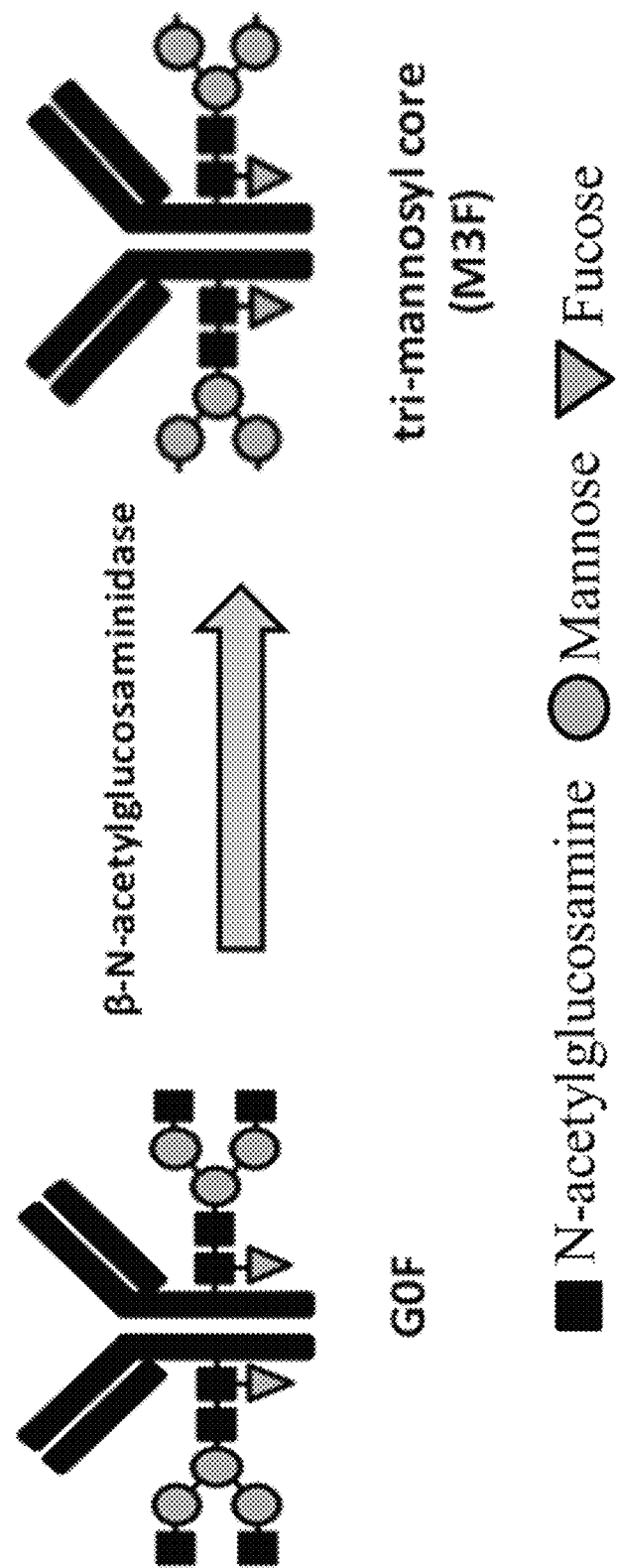
FIG. 17 shows conversion of Herceptin to tri-mannosyl core antibody.
Figure 18:
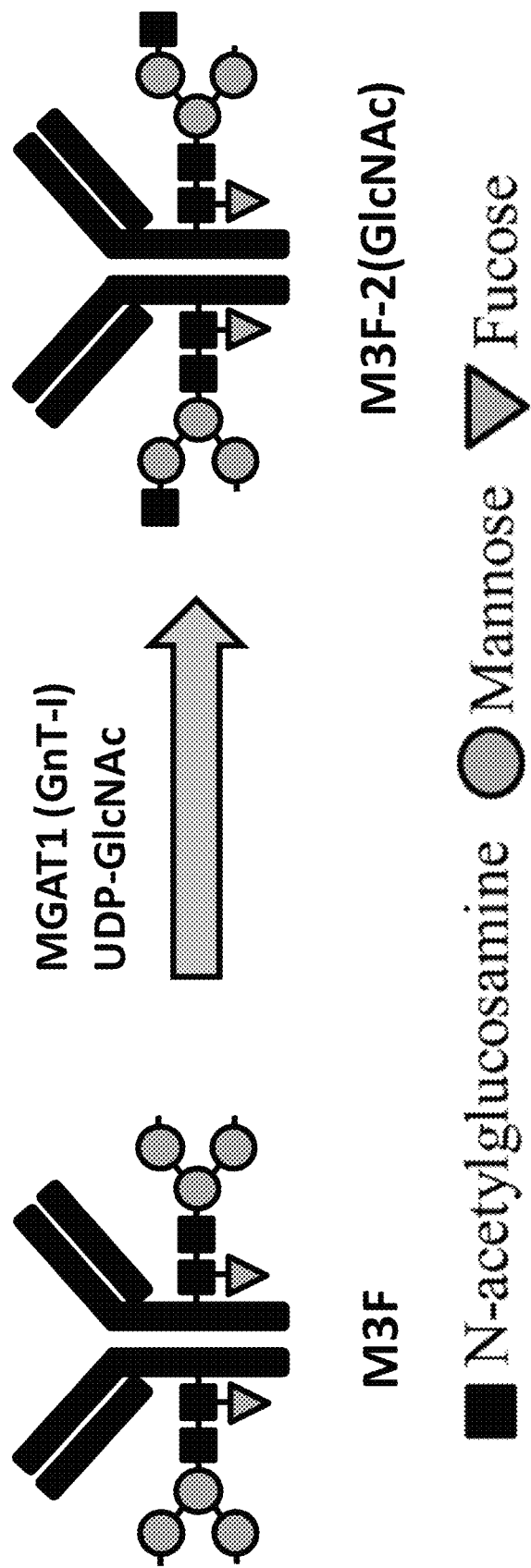
FIG. 18 shows conjugation of GlcNAc to α-3 mannose in one arm of each heavy chain of tri-mannosyl core Herceptin antibody by mannosyl (α-1,3-)-glycoprotein β-1,2-n-acetyl-glucosaminyltransferase (MGAT-1; GnT-1).
Figure 19:
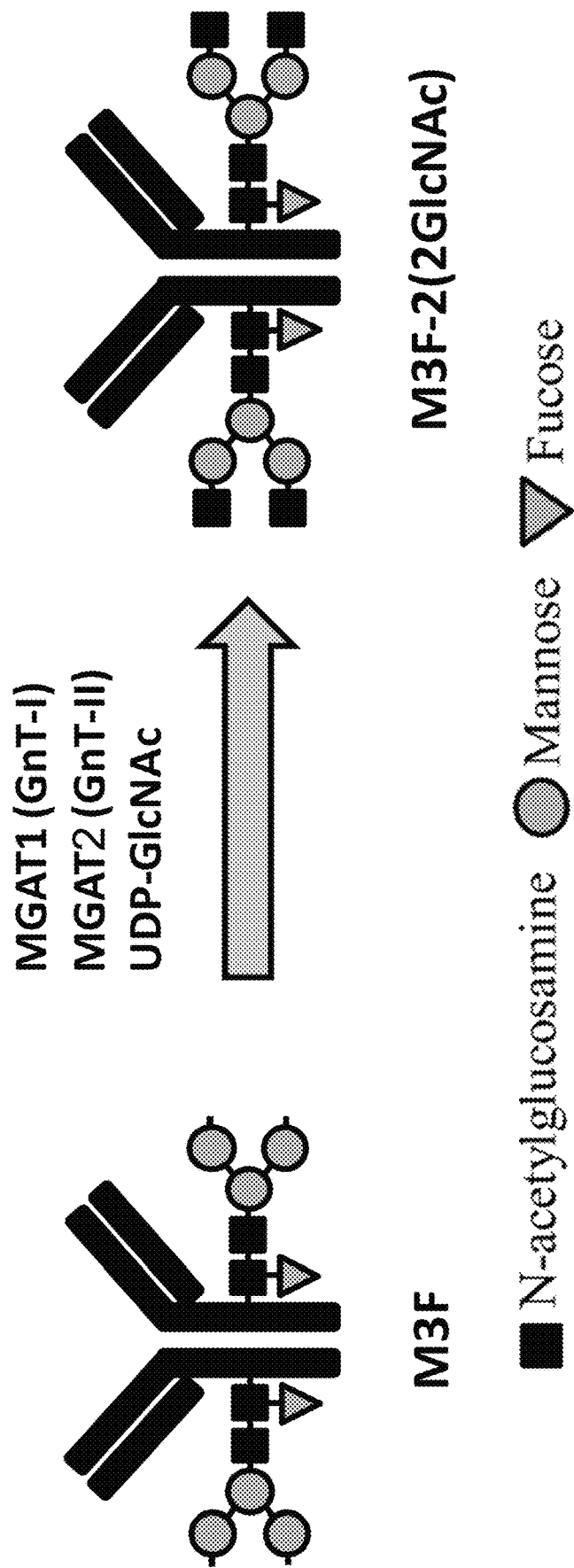
FIG. 19 shows conversion of tri-mannosyl core Herceptin antibody to G0F/G0 Herceptin by MGAT-1 and mannosyl (α-1,6-)-glycoprotein β-1,2-n-acetylglucosaminyltransferase (MGAT-2; GnT-2).
Figure 20:
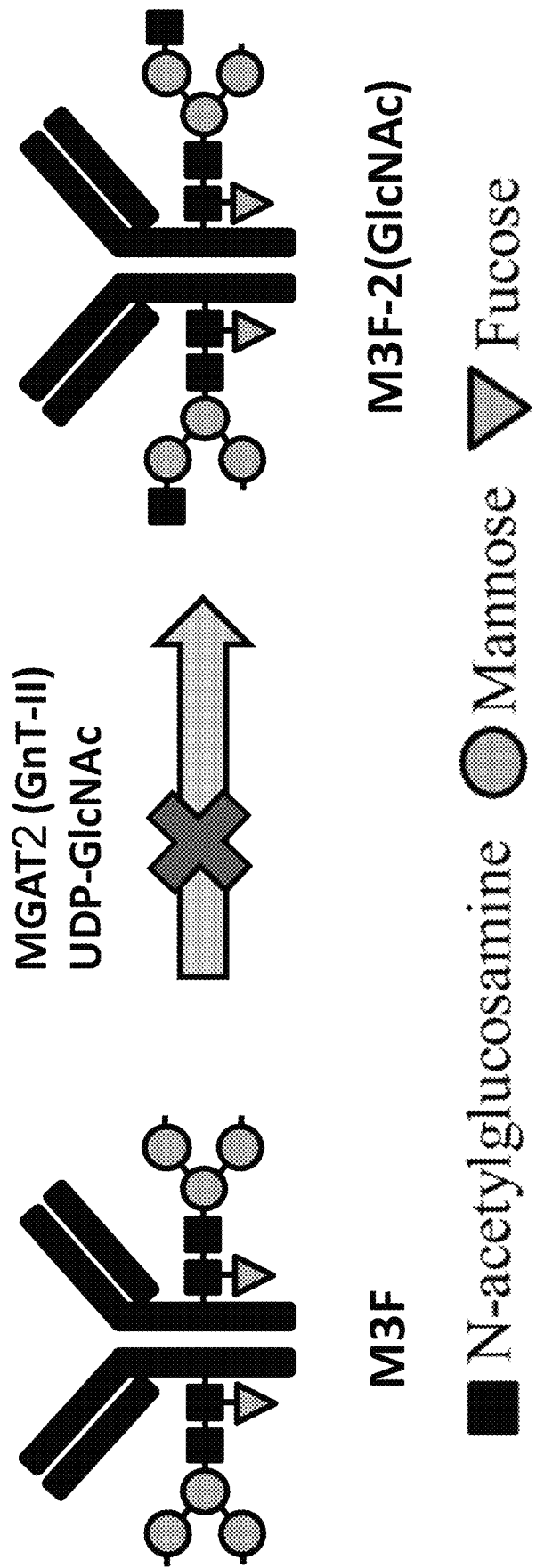
FIG. 20 shows that tri-mannosyl core Herceptin antibody is not a substrate of MGAT-2.
Figure 21:
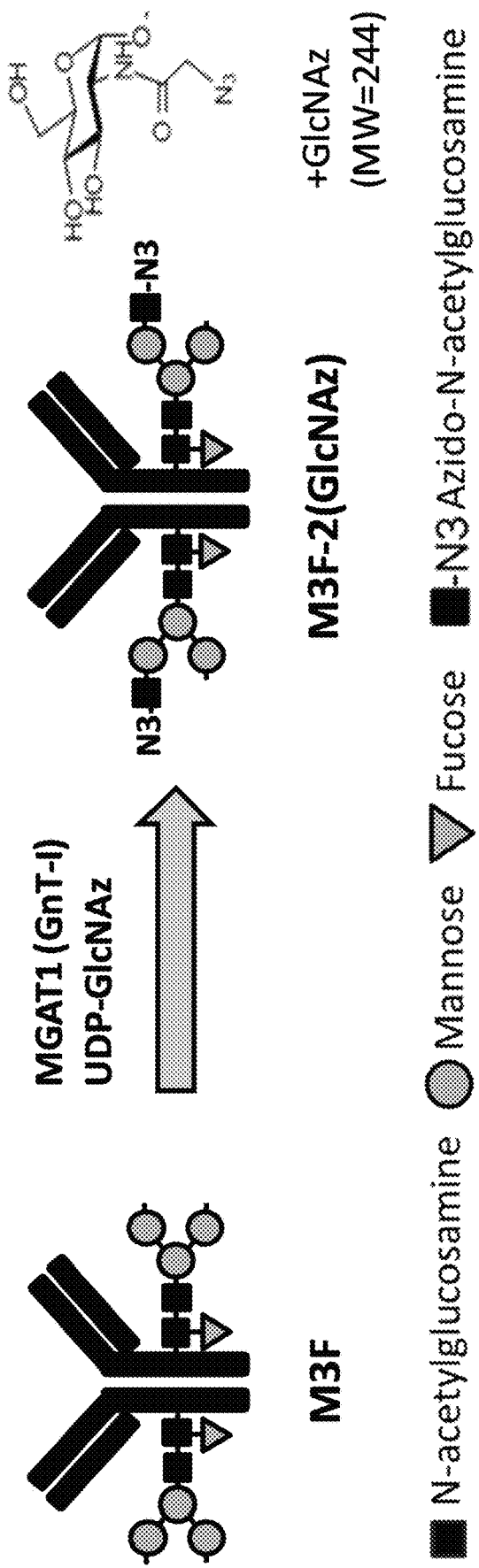
FIG. 21 shows conjugation of GlcNAz to terminal α-3 mannose of one arm of each heavy chain of tri-mannosyl core Herceptin antibody by MGAT-1.
Figure 22:
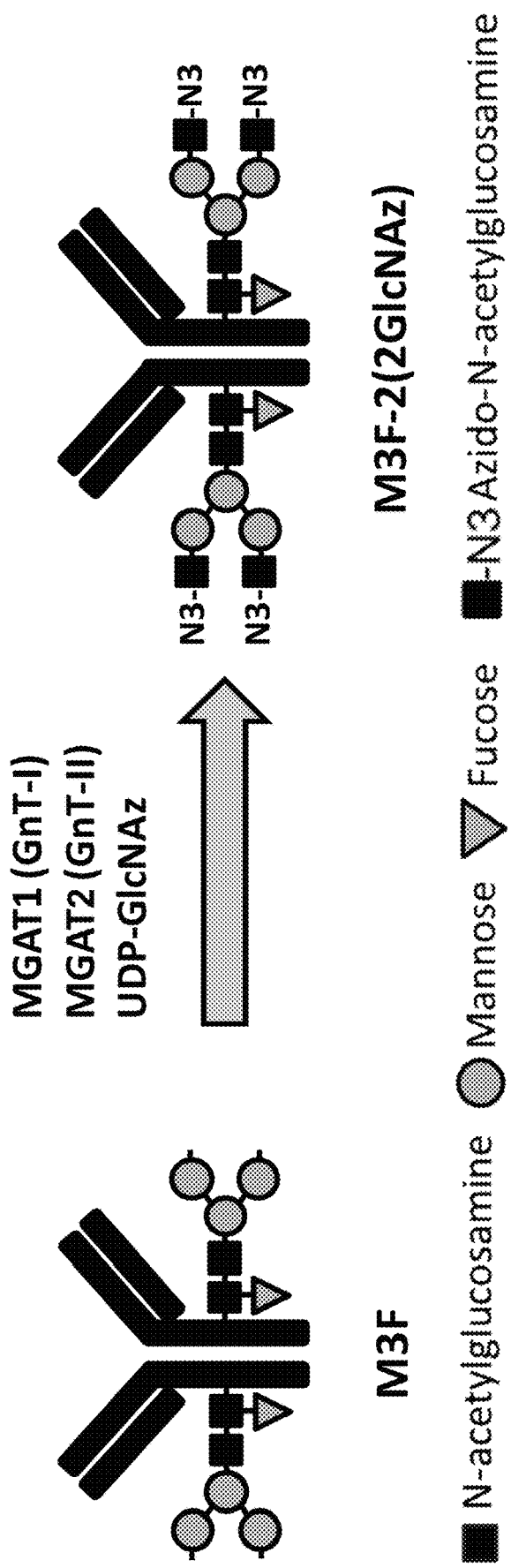
FIG. 22 shows conjugation of UDP-GlcNAz to tri-mannosyl core Herceptin antibody to generate tri-mannosyl Herceptin-4GlcNAz by MGAT-1 and MGAT-2.
Figure 23:
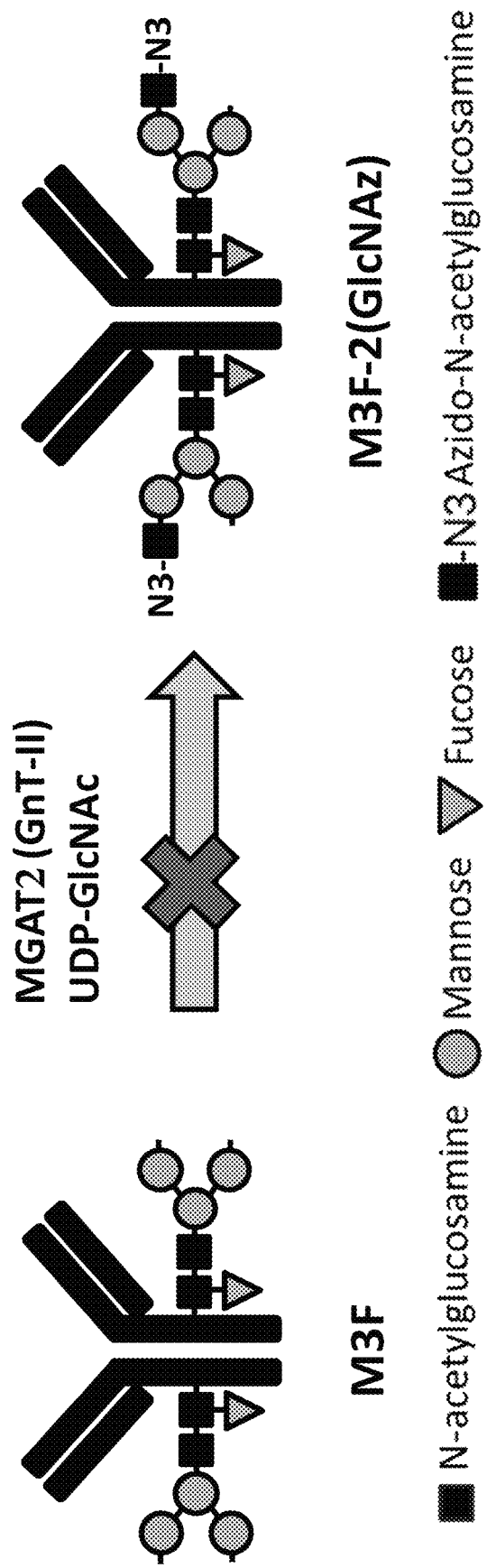
FIG. 23 shows that tri-mannosyl core Herceptin antibody is not a substrate of MGAT-2 to conjugate GlcNAz.
Figure 24:
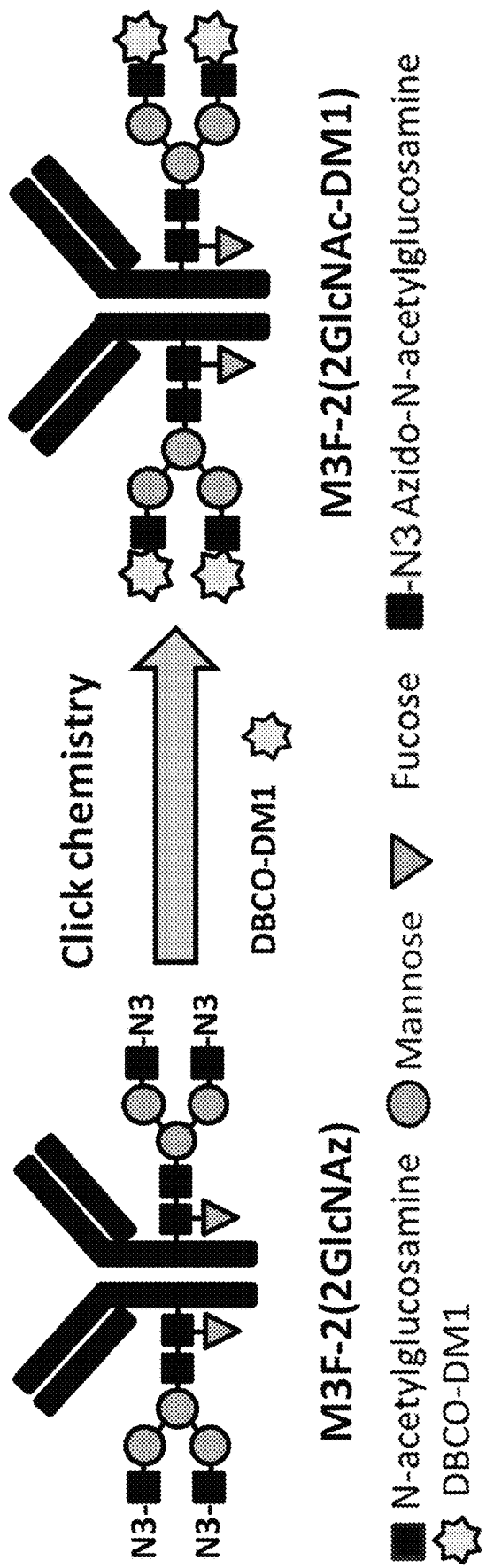
FIG. 24 shows conjugation of tri-mannosyl Herceptin-4GlcNAz antibody with DBCO-(PEG)$_4$-DM1 to produce a Herceptin ADC with DAR4.
Figure 25:
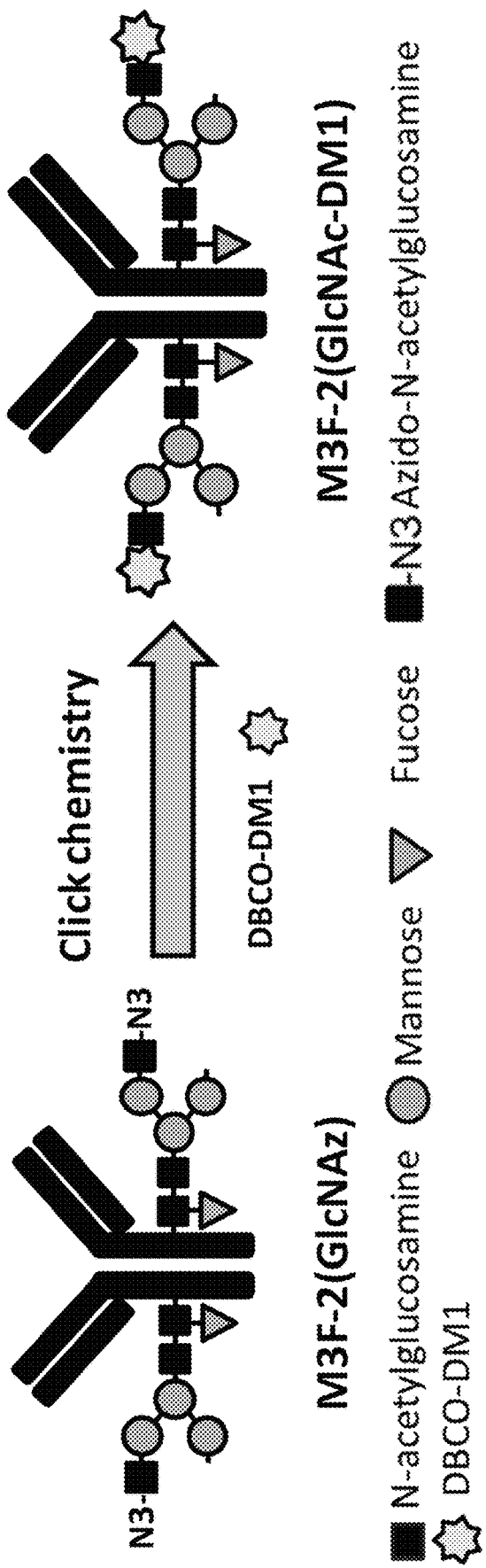
FIG. 25 shows conjugation of a first payload to terminal GlcNAz in each arm of the heavy chains of tri-mannosyl Herceptin-2GlcNAz by DBCO-(PEG)$_4$-DM1.
Figure 26:
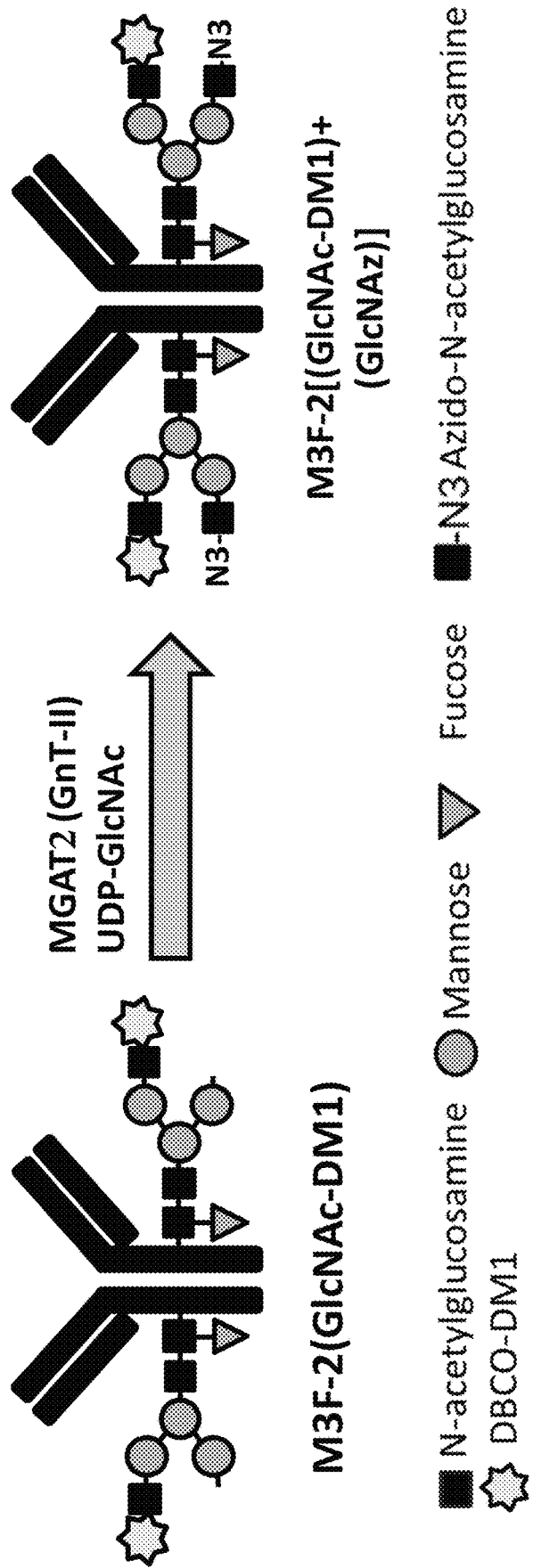
FIG. 26 shows conjugation of a second GlcNAz to terminal α-6 mannose in each arm of the heavy chain of tri-mannosyl Herceptin-2(GlcNAc-triazole-DBCO-(PEG)$_4$-DM1) ADC by MGAT-2.
Figure 27:
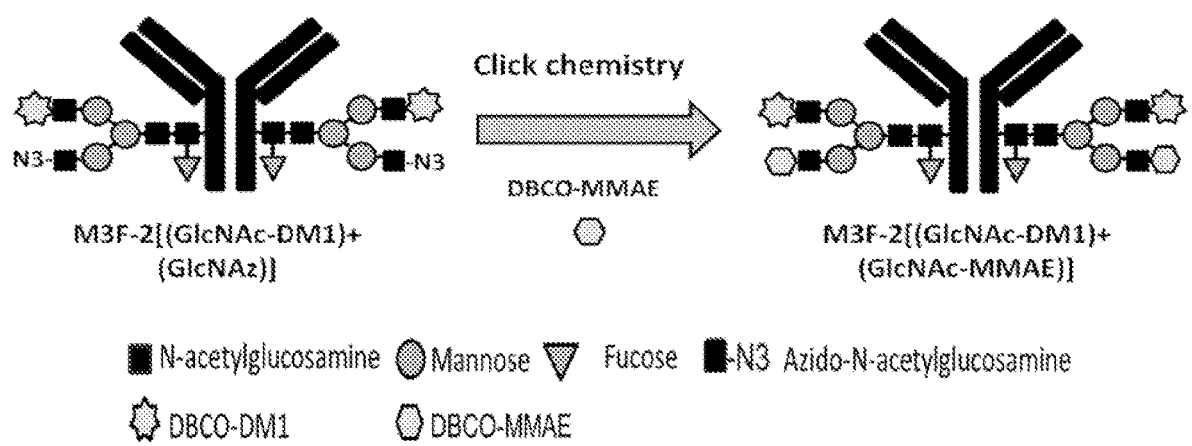
FIG. 27 shows construction of a DAR4 ADC Herceptin product with one MMAE and one DM1 on each arm of the antibody.
Figure 28:
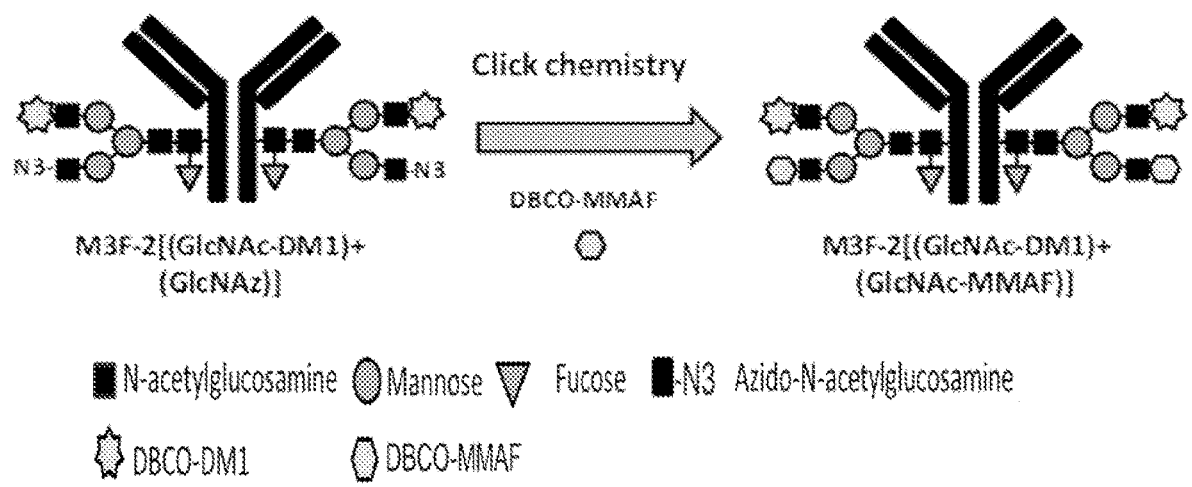
FIG. 28 shows construction of a DAR4 ADC Herceptin product with one MMAF and one DM1 on each arm of the antibody.
Figure 29:
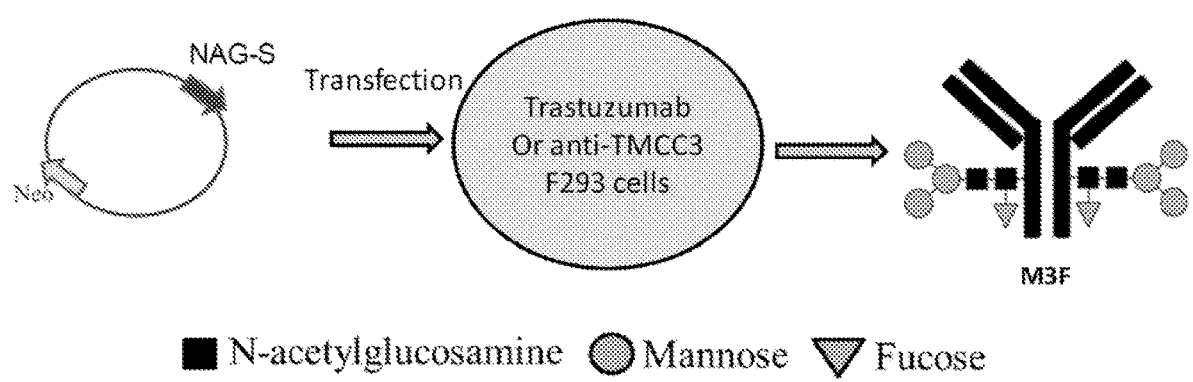
FIG. 29 shows production of tri-mannosyl core Trastuzumab antibody and tri-mannosyl core anti-TMC33 antibody by F293 Cells.

According to the processes described in example 9, DBCO-(PEG)4-DM1 was slowly added to Tris buffer (pH 7.0) containing tri-mannosyl trastuzumab-4GlcNAz antibody obtained above to perform a click chemistry reaction at 25° C. for 16 hours. After reaction and purification, the product was subjected to a reduced mass chromatography analysis and an Intact Mass Chromatography analysis. The Reduced Mass Chromatography analysis results in FIG. 16B reveal that the heavy chain of the product has a molecular weight of 53,509 Da, which implicates that two DBCO-(PEG)$_4$-DM1 molecules (molecular weight of 1,413 Da×2=2,826) have been conjugated to the heavy chain of tri-mannosyl trastuzumab-4GlcNAz antibody. This result is further confirmed from the Intact Mass Chromatography analysis results in the FIG. 16C. This result reveals that a tri-mannosyl-4(GlcNAc-triazole-DBCO-(PEG)$_4$-DM1) ADC product, which contains four DBCO-(PEG)4-DM1 molecules (molecular weight of 1,413 Da×4=5,652 Da) and has a molecular weight of about 153,868 Da, was obtained.

One skilled in the art would readily appreciate that the present invention is well adapted to carry out the objects and obtain the ends and advantages mentioned, as well as those inherent therein. The methods and compositions described herein, as presently representative of preferred embodiments, are exemplary and are not intended as limitations on the scope of the invention. Changes therein and other uses will occur to those skilled in the art, which are encompassed within the spirit of the invention, are defined by the scope of the claims.

What is claimed is:

1. A process for preparing a glycoprotein-payload conjugate comprising a structure of formula (1)

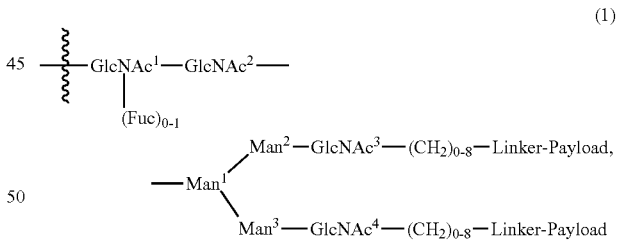

which comprises the steps of:
(i) reacting a glycoprotein comprising a glycan having formula (2)

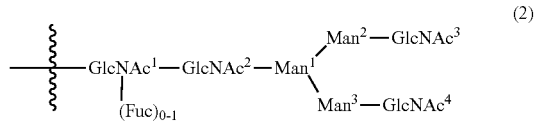

with β-N-acetylglucosaminidase to produce a modified glycoprotein comprising a tri-mannosyl core of formula (3)

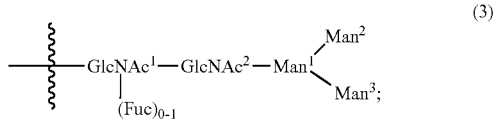

(3)

(ii) reacting the modified glycoprotein comprising the tri-mannosyl core of formula (3) with UDP-GlcNAc-$(CH_2)_{0-8}$—R, wherein R is azido, a ketone group or an aldehyde, in the presence of mannosyl (α-1,3-)-glycoprotein β-1,2-N-acetylglucosaminyltransferase and mannosyl (α-1,6-)-glycoprotein β-1,2-N-acetylglucosaminyltransferase to allow two GlcNAc-$(CH_2)_{0-8}$—R sugars to respectively bond to α-1,2 position of each of $Man^2$ and $Man^3$, and whereby a glycan moiety of formula (4)

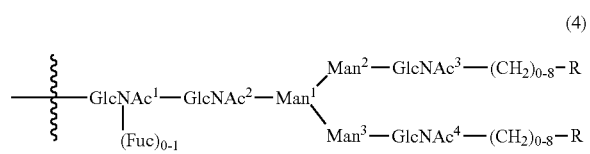

(4)

is formed; and
(iii) reacting two conjugator-linker-payloads, wherein the payloads of the two conjugator-linker-payloads are the same or different, with the glycan moiety of formula (4) to produce the glycoprotein-payload conjugate comprising the structure of formula (1).

2. The process of claim 1, wherein the glycoprotein comprising the glycan having formula (2) in step (i) is produced by a mammalian cell line expressing β-N-acetylglucosaminidase.

3. The process of claim 2, wherein the mammalian cell line is monkey kidney CV1 line transformed by SV40 (COS-7); human embryonic kidney line (293 or 293T cells), baby hamster kidney cells (BHK), mouse sertoli cells (TM4 cells), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells, MRC 5 cells, FS4 cells, Chinese hamster ovary (CHO) cells, or myeloma cell lines.

4. The process of claim 1, wherein the glycoprotein is an antibody or fragment.

5. The process of claim 1, wherein R is an azido, the conjugator is alkynyl, and the reaction performed in step (iii) is click reaction.

6. The process of claim 1, wherein R is a ketone group or an aldehyde, the conjugator is amino, and the reaction performed in step (iii) is reductive amination.

7. The process of claim 1, wherein R is a ketone group or an aldehyde, the conjugator is β-arylethylamino, and the reaction performed in step (iii) is Pictet-Spengler reaction.

8. The process of claim 1, wherein the linker is selected from linear or branched alkyl, cycloalkyl, alkenyl, cycloalkenyl, alkynyl, aryl, heteroaryl, alkoxy, acyl, alkylamines, or arylamine group having 2 to 20 carbon atoms, disulfide containing linkers, acid labile linkers, photolabile linkers, peptidase labile linkers, and esterase labile linkers.

9. The process of claim 1, wherein the payloads are independently selected from a therapeutic agent and a label.

10. The process of claim 9, wherein the therapeutic agent is selected from antimetabolites, alkylating agents, alkylating-like agents, DNA minor groove alkylating agents, anthracyclines, antibiotics, calicheamicins, antimitotic agents, topoisomerase inhibitors, proteasome inhibitors, and radioisotopes.

11. The process of claim 9, wherein the label is a fluorescent label, a chromophoric label, an electron-dense label, a chemiluminescent label, a radioactive label, an enzymatic label, or a positron emitter.

12. A glycoprotein-payload conjugate comprising the structure of formula (1) as defined in claim 1.

13. A process for producing a glycoprotein-payload conjugate comprising a structure of formula (5)

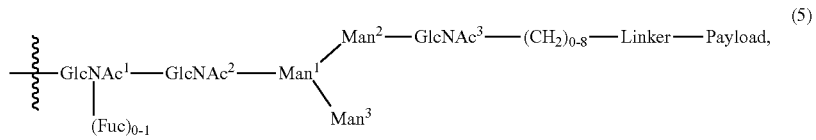

(5)

which comprises the steps of:
(i) reacting the modified glycoprotein comprising the tri-mannosyl core of formula (3) as defined in claim 1 with UDP-GlcNAc-$(CH_2)_{0-8}$—R, wherein R is azido, a ketone group or an aldehyde, in the presence of mannosyl (α-1,3-)-glycoprotein β-1,2-N-acetylglucosaminyltransferase to allow the GlcNAc-$(CH_2)_{0-8}$—R sugar to bond to β-1,2 position of $Man^2$, and whereby a glycoprotein comprising a glycan moiety of formula (6)

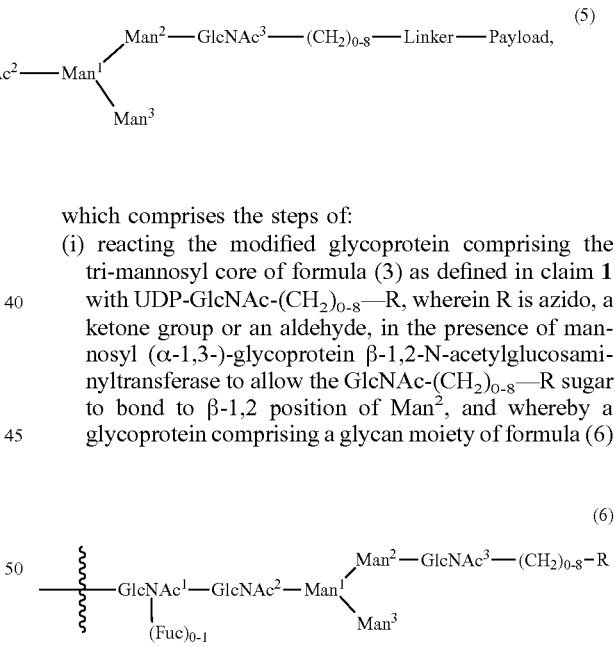

(6)

is formed; and
(ii) reacting a conjugator-linker-payload with the glycoprotein comprising the glycan moiety of formula (6) to produce the glycoprotein-payload conjugate comprising the structure of formula (5).

14. The process of claim 13, wherein the glycoprotein is an antibody or fragment thereof.

15. The process of claim 13 wherein R is azido, the conjugator is alkynyl, and the reaction performed in step (ii) is click reaction.

16. The process of claim 13, wherein R is a ketone group or an aldehyde, the conjugator is amino, and the reaction performed in step (ii) is reductive amination.

17. The process of claim 13, wherein R is a ketone group or an aldehyde, the conjugator is β-arylethylamino, and the reaction performed in step (ii) is Pictet-Spengler reaction.

18. The process of claim 13, wherein the linker is selected from linear or branched alkyl, cycloalkyl, alkenyl, cycloalkenyl, alkynyl, aryl, heteroaryl, alkoxy, acyl, alkylamines, or arylamine group having 2 to 20 carbon atoms, disulfide containing linkers, acid labile linkers, photolabile linkers, peptidase labile linkers, and esterase labile linkers.

19. The process of claim 13, wherein the payload is a therapeutic agent or a label.

20. The process of claim 19, wherein the therapeutic agent is selected from antimetabolites, alkylating agents, alkylating-like agents, DNA minor groove alkylating agents, anthracyclines, antibiotics, calicheamicins, antimitotic agents, topoisomerase inhibitors, proteasome inhibitors, and radioisotopes.

21. The process of claim 19, wherein the label is a fluorescent label, a chromophoric label, an electron-dense label, a chemiluminescent label, a radioactive label, an enzymatic label, or a positron emitter.

22. A glycoprotein-payload conjugate comprising the structure of formula (5) as defined in claim 13.

23. A process for producing a glycoprotein-payload AB conjugate comprising a structure of formula (7)

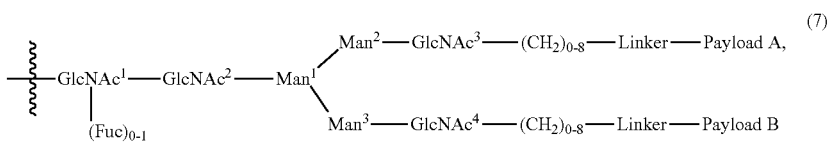

(7)

which comprises the steps of:
(i) reacting the modified glycoprotein comprising the tri-mannosyl core of formula (3) as defined in claim 1 with UDP-GlcNAc-$(CH_2)_{0-8}$—R, wherein R is azido, a ketone group or an aldehyde, in the presence of mannosyl (α-1,3-)-glycoprotein β-1,2-N-acetylglucosaminyltransferase to allow the GlcNAc-$(CH_2)_{0-8}$—R sugar to bond to β-1,2 position of $Man^2$, and whereby a glycoprotein comprising a glycan moiety of formula (6)

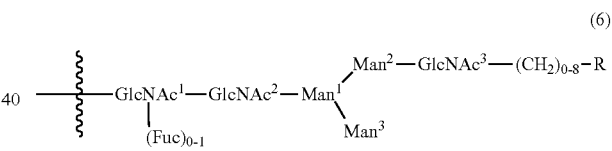

(6)

is formed;
(ii) reacting a conjugator-linker-payload A with the glycoprotein comprising the glycan moiety of formula (6) to produce a glycoprotein-payload A conjugate comprising the structure of formula (8)

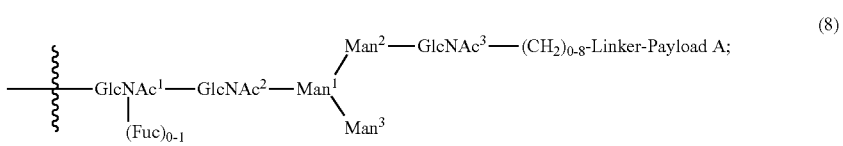

(8)

(iii) reacting the glycoprotein-payload A conjugate comprising the structure of formula (8) with UDP-GlcNAc-$(CH_2)_{0-8}$—R, wherein R is azido, a ketone group or an aldehyde, in the presence of mannosyl (α-1,6-)-glycoprotein β-1,2-N-acetylglucosaminyltransferase to allow the GlcNAc-$(CH_2)_{0-8}$—R sugar to bond to β-1,2 position of $Man^3$, and whereby a glycoprotein comprising a glycan-payload A moiety having formula (9)

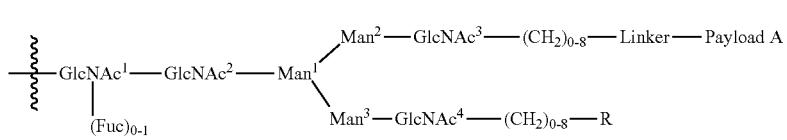

is formed; and (iv) reacting a conjugator-linker-payload B with the glycoprotein comprising the glycan-payload A moiety having formula (9) to produce the glycoprotein-payload A/B conjugate comprising the structure of formula (7), wherein the payload A and the payload B are the same or different.

24. The process of claim 23, wherein the glycoprotein is an antibody or fragment thereof.

25. The process of claim 23, wherein R is azido, the conjugator is alkynyl, and the reaction performed in step (ii) and/or step (iv) is click reaction.

26. The process of claim 23, wherein R is a ketone group or an aldehyde, the conjugator is amino, and the reaction performed in step (ii) and/or step (iv) is reductive amination.

27. The process of claim 23, wherein R is a ketone group or an aldehyde, the conjugator is β-arylethylamino, and the reaction performed in step (ii) and/or step (iv) is Pictet-Spengler reaction.

28. The process of claim 23, wherein the linker is selected from linear or branched alkyl, cycloalkyl, alkenyl, cycloalkenyl, alkynyl, aryl, heteroaryl, alkoxy, acyl, alkylamines, or arylamine group having 2 to 20 carbon atoms, disulfide containing linkers, acid labile linkers, photolabile linkers, peptidase labile linkers, and esterase labile linkers.

29. The process of claim 23, wherein the payload A and the payload B are independently selected from a therapeutic agent and a label.

30. The process of claim 29, wherein the therapeutic agent is selected from antimetabolites, alkylating agents, alkylating-like agents, DNA minor groove alkylating agents, anthracyclines, antibiotics, calicheamicins, antimitotic agents, topoisomerase inhibitors, proteasome inhibitors, and radioisotopes.

31. The process of claim 29, wherein the label is a fluorescent label, a chromophoric label, an electron-dense label, a chemiluminescent label, a radioactive label, an enzymatic label, or a positron emitter.

32. A glycoprotein-payload AB conjugate comprising the structure of formula (7) as defined in claim 23.

33. The process of claim 1, wherein in step (i) the glycoprotein comprises the glycan having formula (2) and a protein, the glycan being attached to a hydroxyl group of the protein, to an amide on the protein or to a carbon on the protein.

34. The process of claim 4, wherein the glycoprotein is an antibody Fab fragment, F(ab')2, Fv fragment or Fc fragment from a cleaved antibody, an scFv-Fc fragment, a minibody, a diabody or an scFv.

35. The process of claim 14, wherein the glycoprotein is an antibody Fab fragment, F(ab')2, Fv fragment or Fc fragment from a cleaved antibody, an scFv-Fc fragment, a minibody, a diabody or an scFv.

36. The process of claim 24, wherein the glycoprotein is an antibody Fab fragment, F(ab')2, Fv fragment or Fc fragment from a cleaved antibody, an scFv-Fc fragment, a minibody, a diabody or an scFv.

* * * * *